US011534205B2

(12) United States Patent
Reid et al.

(10) Patent No.: US 11,534,205 B2
(45) Date of Patent: *Dec. 27, 2022

(54) CANNULA SEAL ASSEMBLY

(71) Applicant: Intuitive Surgical Operations, Inc., Sunnyvale, CA (US)

(72) Inventors: Robert C Reid, Fairfield, CT (US); Justin Krom, Southington, CT (US); Tyler J. Morrissette, Niantic, CT (US); Joseph P. Orban, III, Norwalk, CT (US); William A. Burbank, Sandy Hook, CT (US); David DeTroy, Norwalk, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 16/592,406

(22) Filed: Oct. 3, 2019

(65) Prior Publication Data

US 2020/0100815 A1 Apr. 2, 2020

Related U.S. Application Data

(63) Continuation of application No. 15/126,968, filed as application No. PCT/US2015/020887 on Mar. 17, 2015, now Pat. No. 10,463,395.

(Continued)

(51) Int. Cl.
*A61B 17/34* (2006.01)
*A61B 17/02* (2006.01)
*A61B 34/30* (2016.01)

(52) U.S. Cl.
CPC ...... *A61B 17/3462* (2013.01); *A61B 17/0218* (2013.01); *A61B 17/3423* (2013.01);
(Continued)

(58) Field of Classification Search
CPC ........ A61B 17/3462; A61B 2017/3419; A61B 2017/3464
See application file for complete search history.

(56) References Cited

U.S. PATENT DOCUMENTS 4,655,752 A 4/1987 Honkanen et al.
4,929,235 A 5/1990 Merry et al.
(Continued)

FOREIGN PATENT DOCUMENTS

CN 101478924 A 7/2009
CN 106255469 A 12/2016
(Continued)

OTHER PUBLICATIONS

Extended European Search Report for Application No. EP20174147.7, dated Oct. 1, 2020, 5 pages.
(Continued)

*Primary Examiner* — Andrew Yang
(74) *Attorney, Agent, or Firm* — Schwegman Lundberg & Woessner, P.A.

(57) ABSTRACT

Gas-tight seal assemblies for us during minimally invasive surgery include various aspects. A wiper seal includes a sealing portion and a surrounding flex portion. Upper and lower faces of the sealing portions are angled with reference to an inserted instrument, the upper face's angle being more acute with reference to the instrument's shaft than the lower face's angle. The flex portion is corrugated, support ribs are in one or more corrugation grooves, and the support ribs allow the groove to easily collapse but resist the groove widening. The support ribs also prevent the sealing portion from inverting. An instrument insertion guide is positioned over the sealing portion and moves laterally with the sealing portion. A latch piece removably secures the seal assembly to a cannula. An anti-inversion piece prevents the wiper seal from inverting when an instrument is withdrawn. An assem-
(Continued)

bly may include various combinations of the seal assembly, a cannula, a surgical instrument, an obturator, an endoscope, and a teleoperated medical device. The seal assembly may rotate within a cannula. The seal assembly may be used during manual or teleoperated surgery.

20 Claims, 32 Drawing Sheets

Related U.S. Application Data

(60) Provisional application No. 61/954,227, filed on Mar. 17, 2014.

(52) U.S. Cl.
CPC .......... *A61B 17/3498* (2013.01); *A61B 34/30* (2016.02); *A61B 2017/3464* (2013.01)

(56) References Cited

U.S. PATENT DOCUMENTS

| | | |
|---|---|---|
| 5,197,955 A | 3/1993 | Stephens et al. |
| 5,209,737 A | 5/1993 | Ritchart et al. |
| 5,300,036 A | 4/1994 | Mueller et al. |
| 5,304,143 A | 4/1994 | Green et al. |
| 5,308,336 A | 5/1994 | Hart et al. |
| 5,312,363 A | 5/1994 | Ryan et al. |
| 5,350,364 A | 9/1994 | Stephens et al. |
| 5,354,280 A | 10/1994 | Haber et al. |
| 5,360,417 A | 11/1994 | Gravener et al. |
| 5,385,553 A | 1/1995 | Hart et al. |
| 5,391,153 A | 2/1995 | Haber et al. |
| 5,391,154 A | 2/1995 | Young |
| 5,407,433 A | 4/1995 | Loomas |
| 5,411,483 A | 5/1995 | Loomas et al. |
| 5,437,646 A | 8/1995 | Hunt et al. |
| 5,492,304 A | 2/1996 | Smith et al. |
| 5,496,280 A | 3/1996 | Vandenbroek et al. |
| 5,542,931 A | 8/1996 | Gravener et al. |
| 5,628,732 A | 5/1997 | Antoon, Jr. et al. |
| 5,685,854 A | 11/1997 | Green et al. |
| 5,720,730 A | 2/1998 | Blake, III |
| 5,720,759 A | 2/1998 | Green et al. |
| 5,722,958 A | 3/1998 | Gravener et al. |
| 5,727,770 A | 3/1998 | Dennis |
| 5,752,938 A | 5/1998 | Flatland et al. |
| 5,782,817 A | 7/1998 | Franzel et al. |
| 5,788,676 A | 8/1998 | Yoon |
| 5,814,026 A | 9/1998 | Yoon |
| 5,820,600 A | 10/1998 | Carlson et al. |
| 5,820,604 A | 10/1998 | Fox et al. |
| 5,865,807 A | 2/1999 | Blake, III |
| 5,989,233 A | 11/1999 | Yoon |
| 6,093,176 A | 7/2000 | Dennis |
| 6,127,320 A | 10/2000 | Van et al. |
| 6,159,182 A | 12/2000 | Davis et al. |
| 6,228,061 B1 | 5/2001 | Flatland et al. |
| 6,258,065 B1 | 7/2001 | Dennis et al. |
| 6,482,181 B1 | 11/2002 | Racenet et al. |
| 6,551,282 B1 | 4/2003 | Exline et al. |
| 6,595,946 B1 | 7/2003 | Pasqualucci |
| 6,702,787 B2 | 3/2004 | Racenet et al. |
| 6,726,663 B1 | 4/2004 | Dennis |
| 7,083,626 B2 | 8/2006 | Hart et al. |
| 7,112,185 B2 | 9/2006 | Hart et al. |
| 7,153,319 B1 | 12/2006 | Haberland et al. |
| 7,235,062 B2 | 6/2007 | Brustad |
| 7,591,802 B2 | 9/2009 | Johnson et al. |
| 7,722,570 B2 | 5/2010 | Almond et al. |
| 7,988,671 B2 | 8/2011 | Albrecht et al. |
| 8,012,128 B2 | 9/2011 | Franer et al. |
| 8,147,458 B2 | 4/2012 | Hart et al. |
| 8,152,773 B2 | 4/2012 | Albrecht et al. |
| 8,192,405 B2 | 6/2012 | Racenet et al. |
| 8,273,060 B2 | 9/2012 | Moreno et al. |
| 10,463,395 B2 | 11/2019 | Reid et al. |
| 2002/0013552 A1 | 1/2002 | Dennis |
| 2003/0004529 A1 | 1/2003 | Tsonton et al. |
| 2004/0066008 A1 | 4/2004 | Smith |
| 2004/0260244 A1 | 12/2004 | Piechowicz et al. |
| 2005/0131349 A1 | 6/2005 | Albrecht et al. |
| 2005/0209608 A1 | 9/2005 | O'Heeron |
| 2006/0047293 A1 | 3/2006 | Haberland et al. |
| 2006/0264991 A1 | 11/2006 | Johnson et al. |
| 2006/0276751 A1 | 12/2006 | Haberland et al. |
| 2007/0088277 A1 | 4/2007 | Mcginley et al. |
| 2007/0244426 A1 | 10/2007 | Hart et al. |
| 2007/0255218 A1 | 11/2007 | Franer |
| 2008/0171987 A1 | 7/2008 | Franer et al. |
| 2009/0012476 A1 | 1/2009 | Catlin |
| 2010/0004599 A1 | 1/2010 | Zhou et al. |
| 2010/0270751 A1 | 10/2010 | Loe et al. |
| 2010/0280456 A1 | 11/2010 | Nijland et al. |
| 2012/0004613 A1 | 1/2012 | Franer |
| 2012/0089094 A1 | 4/2012 | Franer et al. |
| 2012/0108905 A1 | 5/2012 | Carter et al. |
| 2014/0018631 A1 | 1/2014 | Kleyman |
| 2014/0074035 A1 | 3/2014 | Detroy et al. |
| 2017/0095269 A1 | 4/2017 | Reid et al. |

FOREIGN PATENT DOCUMENTS

| | | |
|---|---|---|
| EP | 0627233 A2 | 12/1994 |
| EP | 2656802 A1 | 10/2013 |
| JP | 2010520974 A | 6/2010 |
| WO | WO-9952577 A1 | 10/1999 |
| WO | WO-2009119053 A1 | 10/2009 |
| WO | WO-2011037718 A1 | 3/2011 |
| WO | WO-2011060046 A2 | 5/2011 |
| WO | WO-2012144846 A2 | 10/2012 |

OTHER PUBLICATIONS

Extended European Search Report for Application No. EP20174165.9, dated Oct. 1, 2020, 8 pages.
Extended European Search Report for EP Application No. 20174141.0, dated Oct. 2, 2020, 6 pages.
"U.S. Appl. No. 15/126,968, Advisory Action dated Feb. 13, 2019", 3 pgs.
"U.S. Appl. No. 15/126,968, Examiner Interview Summary dated Jan. 30, 2019", 3 pgs.
"U.S. Appl. No. 15/126,968, Final Office Action dated Dec. 6, 2018", 7 pgs.
"U.S. Appl. No. 15/126,968, Non Final Office Action dated Feb. 25, 2019", 7 pgs.
"U.S. Appl. No. 15/126,968, Non Final Office Action dated Aug. 9, 2018", 8 pgs.
"U.S. Appl. No. 15/126,968, Notice of Allowance dated Jun. 26, 2019", 6 pgs.
"U.S. Appl. No. 15/126,968, Response filed May 28, 2019 to Non Final Office Action dated Feb. 25, 2019", 8 pgs.
"U.S. Appl. No. 15/126,968, Response to Final Office Action dated Dec. 6, 2018 filed Feb. 6, 2019", 13 pgs.
"U.S. Appl. No. 15/126,968, Response to Non Final Office Action dated Aug. 9, 2018 filed Nov. 5, 2018", 13 pgs.
"Chinese Application Serial No. 201580020656.2, Office Action dated Jul. 11, 2018", W/English Translation, 5 pgs.
"Chinese Application Serial No. 201580020656.2, Office Action dated Aug. 15, 2019", 6 pgs.
"Chinese Application Serial No. 201580020656.2, Office Action dated Nov. 8, 2018", w/English translation, 17 pgs.
"Chinese Application Serial No. 201580020656.2, Response filed Apr. 11, 2019 to Office Action dated Nov. 8, 2018", w/ English claims, 9 pgs.
"Chinese Application Serial No. 201580020656.2, Response filed Sep. 11, 2018 to Office Action dated Jul. 11, 2018", W/English Translated Claims, 14 pgs.

(56) References Cited

OTHER PUBLICATIONS

"European Application Serial No. 15765490.6, Extended European Search Report dated Feb. 13, 2018", 13 pgs.
"European Application Serial No. 15765490.6, Partial Supplementary European Search Report dated Oct. 12, 2017", 15 pgs.
"International Application Serial No. PCT/US2015/020887, International Search Report dated Jun. 5, 2015", 4 pgs.
"International Application Serial No. PCT/US2015/020887, Written Opinion dated Jun. 5, 2015", 9 pgs.
"Japanese Application Serial No. 2016-557657, Notification of Reasons for Refusal dated Jan. 29, 2019", 7 pgs.
"Japanese Application Serial No. 2016-557657, Response filed May 9, 2019 to Notification of Reasons for Refusal dated Jan. 29, 2019", w/o English claims, 5 pgs.

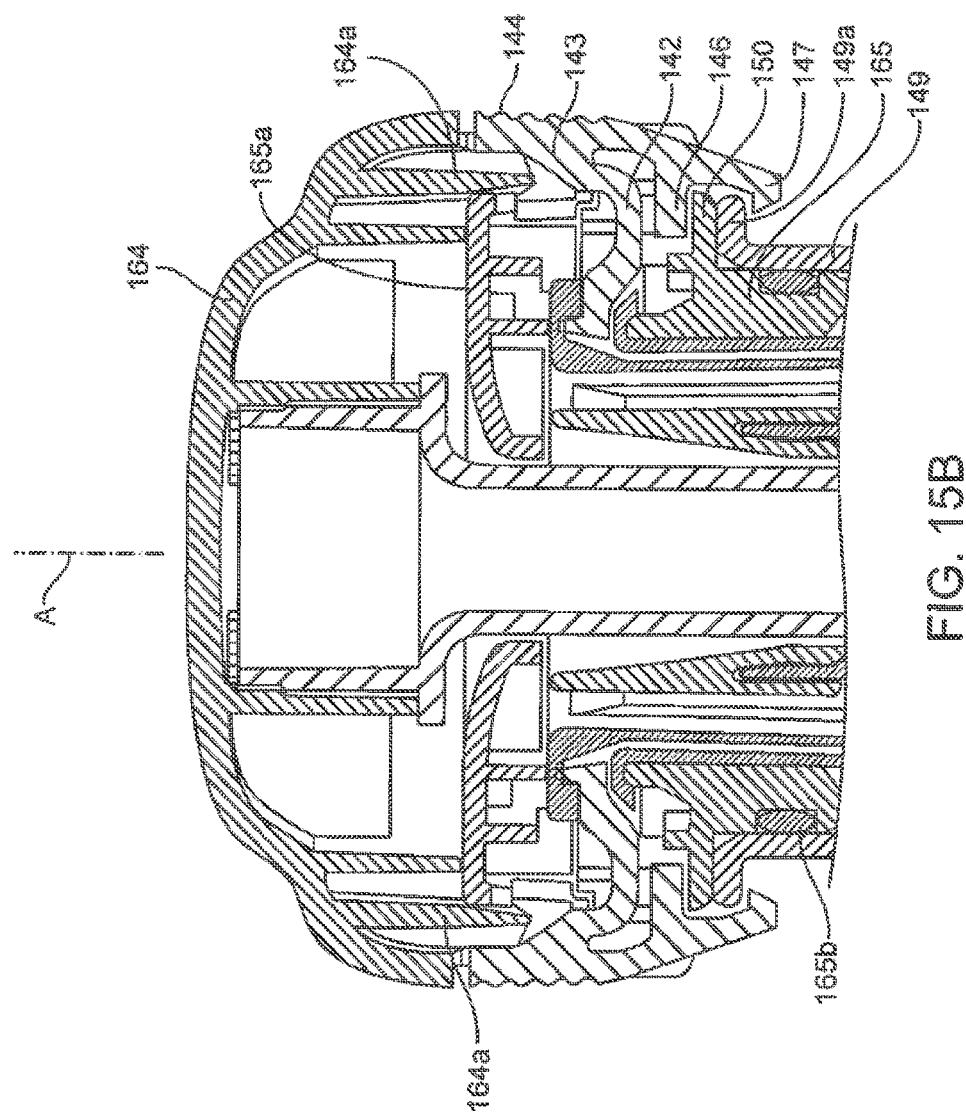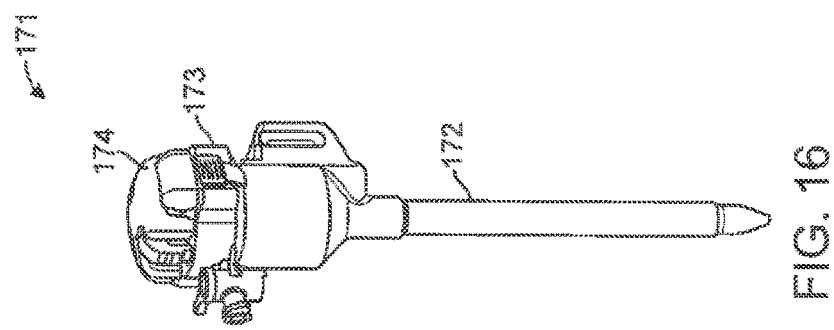

CANNULA SEAL ASSEMBLY

CROSS-REFERENCE TO RELATED APPLICATIONS

This application is a continuation of U.S. patent application Ser. No. 15/126,968, filed Sep. 16, 2016, which is a U.S. National Stage Filing under 35 U.S.C. 371 from International Application No. PCT/US2015/020887, filed on Mar. 17, 2015, and published as WO 2015/142794 A1 on Sep. 24, 2015, which claims the benefit of U.S. Provisional Patent Application No. 61/954,227 (filed Mar. 17, 2014), each of which is incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not applicable.

BACKGROUND

1. Field of Invention

Inventive aspects relate in general to medical devices, and more specifically to cannula seals for minimally invasive surgical systems.

2. Art

In minimally invasive surgery, a body cavity is often insufflated to provide additional work room at the surgical site. In order to prevent insufflation gas from escaping through the cannulas that guide minimally invasive surgical instruments into the body, one or more gas-tight seals are typically coupled to the cannula. These gas-tight seals prevent insufflation gas from escaping through an open cannula when no surgical instrument is inserted through the cannula, and they also prevent gas from escaping through the gap between the cannula and instrument shaft when a surgical instrument is inserted through the cannula.

U.S. Pat. No. 6,123,689 (filed Mar. 28, 1997) discloses a "Reusable Cannula with Disposable Seal," which is an example of a device that performs the basic functions a minimally invasive surgery cannula seal assembly requires. Two annular flanges provide a gas-tight seal against instrument shafts of various diameters inserted through the seal assembly, and a trap door closes to provide a gas-tight seal when the instrument is removed from the seal assembly. An adapter portion may be coupled over the seal assembly to seal against instrument shafts having a diameter smaller than the shaft diameters sealed by the annular flanges. Instrument shafts include shafts used for endoscopes and other surgical accessories, such as obturators.

Although current cannula seals for minimally invasive surgery are generally effective, improvements are desirable. Such improvements include an increased resistance against punctures and tears that may occur as surgical instruments are inserted through the seal and which reduce or prevent effective sealing (especially for thin-membrane, septum-type wiper seals), an effective accommodation of instrument shafts over a wide range of shaft diameters to minimize the need for two or more seals and consequently reduce operating costs, reduced friction against the instrument shaft as it inserts and withdraws through the seal (thus allowing instruments to be teleoperatively controlled with increased precision, allowing more accurate insertion/withdrawal axis force feedback to a teleoperating surgeon by reducing any other forces along the insertion/withdrawal axis, and reducing a tendency for the seal to invert as the instrument shaft reciprocates), reduced part costs, easy and economical manufacturability, and easy assembly both during manufacturing and in use during surgery.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its purpose is to present some aspects and embodiments in a general form as a prelude to the more detailed description below.

In one aspect, a wiper seal includes features that prevent the seal from inverting as a surgical instrument passes through the seal.

In one aspect, a wiper seal includes features that provide relatively higher friction against a surgical instrument shaft being inserted through the seal, and relatively lower friction against a surgical instrument shaft being withdrawn through the seal.

In one aspect, an instrument insertion guide extends from a top of a seal assembly housing distally to an underlying wiper seal to help guide a surgical instrument tip through the seal without damaging the seal.

In one aspect, an instrument insertion guide is coupled to the top of a wiper seal to help guide a surgical instrument tip through the seal without damaging the seal.

In one aspect, a seal assembly includes a single latch piece that removably secures the seal assembly to a cannula bowl.

In one aspect, a seal assembly includes an anti-inversion feature that prevents a seal from being pulled proximally as a surgical instrument is withdrawn through the seal.

In one aspect, a seal is maintained between a seal assembly and a cannula as the seal assembly rotates within the cannula's bowl.

These and other aspects are described in more detail below.

BRIEF DESCRIPTION OF THE DRAWINGS

FIGS. 3C-3AB are top and perspective views of various wiper seal support rib configurations.

FIG. 15B is a cross-sectional view taken at right angles to the view in FIG. 15A.

FIG. 16 is a perspective view of a medical device assembly that includes a cannula, a seal assembly latched to the cannula, and an obturator latched to seal assembly.

DETAILED DESCRIPTION

Figure 1:
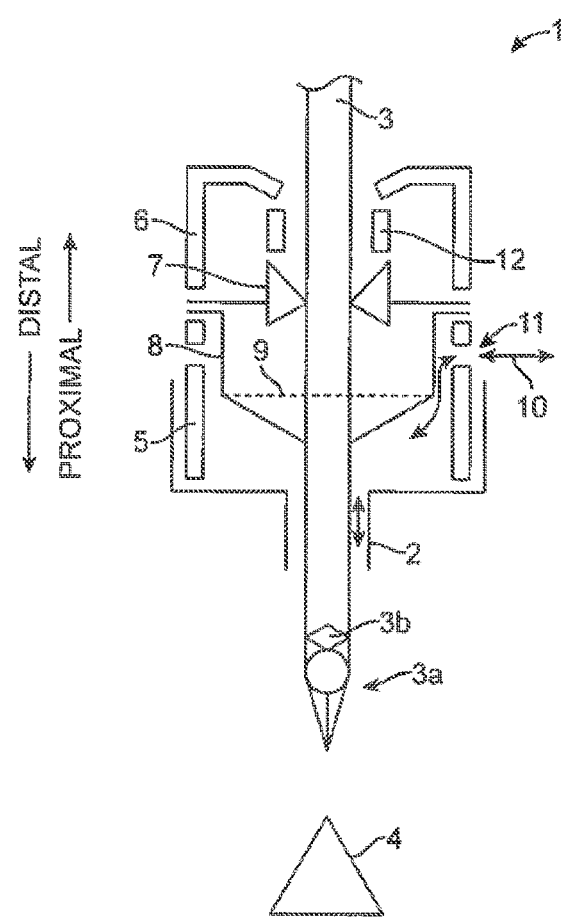
FIG. 1 is a diagrammatic, cross-sectional view of a seal assembly.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements. Headings are to assist the reader, and they form no portion of the description.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations in space) and orientations (i.e., rotational placements in space) of a device in use or operation, in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. Also, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not exclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOFs). Examples of such parts include closed, bendable tubes (made from, e.g., NITINOL, polymer, soft rubber, and the like) and helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae". In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Aspects of the invention are described primarily in terms of an implementation using a da Vinci® Surgical System commercialized by Intuitive Surgical, Inc. of Sunnyvale, Calif. Knowledgeable persons will understand, however, that inventive aspects disclosed herein may be embodied and implemented in various ways, including teleoperated and, if applicable, non-teleoperated embodiments and implementations. Implementations on da Vinci® Surgical Systems are merely exemplary and are not to be considered as limiting the scope of the inventive aspects disclosed herein.

Seal Assembly

FIG. 1 is a diagrammatic, cross-sectional view of a seal assembly 1 for a minimally invasive surgical instrument. Proximal and distal orientation directions are as depicted as indicated by the arrows, and these orientations generally apply throughout this description and the associated figures. As shown in FIG. 1, seal assembly 1 is positioned in the proximal end of cannula 2 (typically within a cannula bowl at the cannula's proximal end), and a portion of minimally invasive surgical instrument 3 is shown extending through seal assembly 1 and cannula 2 towards a surgical site 4 within a patient body. Surgical instrument 3 may optionally include various distal end components, such a surgical end effector 3a having one or more mechanical DOFs and a wrist mechanism 3b with one or more mechanical DOFs that allows a surgeon to change end effector 3a's orientation. Surgical instrument 3 typically inserts distally and withdraws proximally (i.e., reciprocates) through seal assembly 1 and cannula 2 many times as a surgeon operates the instrument during a surgical procedure. A latch piece (not shown) holds seal assembly 1 in place with reference to cannula 2, as described in detail below.

As shown, seal assembly 1 includes a lower housing 5 and an upper housing 6 that when assembled together form a seal assembly housing. Lower housing 5 and upper housing 6 are shown as two separate pieces that are joined to make a complete single housing, and optionally the complete seal assembly housing is formed as a single piece. Seal assembly 1 further includes a wiper seal 7 and a fluid (e.g., gas, liquid) backflow prevention seal 8. Several wiper seal 7 embodiments are described in detail below. Backflow prevention seal 8 may optionally be one of several forms of seals in which one or more slits are held closed (by inherent elastomeric material properties and by fluid pressure against the distal side of the seal) to prevent fluid backflow through the seal, but which are opened to allow fluid or an object to pass through the seal. Such seals include a single-slit "duckbill" form, an intersecting three-slit trifold form, an intersecting two-slit (a.k.a. "cross-slit" or "cruciform") form, and an S-curved form. Other backflow prevention type seals may be used (e.g., trap doors, check valves, and the like).

In use, backflow prevention seal 8 closes as shown by the dashed line alternate position 9, which prevents surgical insufflation gas or other fluid from escaping through the cannula when no surgical instrument is inserted into the cannula. When a surgical instrument is inserted into the cannula, backflow prevention seal 8 opens, and wiper seal 7 seals against the surgical instrument's shaft to likewise prevent insufflation gas or other fluid from escaping through the cannula. Thus wiper seal 7 and backflow prevention seal 8 cooperate to prevent insufflation gas or other fluid from escaping though the cannula during a surgical procedure, regardless of whether a surgical instrument is inserted into the cannula.

As shown in FIG. 1, wiper seal 7 and backflow prevention seal 8 are sandwiched between lower housing 5 and upper housing 6, although other configurations to hold the seals inside the seal assembly housing are possible, such as by the use of adhesive or other means of fixing the seals inside the housing. One or more optional spacers (not shown) may also be sandwiched between the upper and lower housings, as described below.

FIG. 1 further illustrates that seal assembly 1 may be configured to allow insufflation gas to enter the patient and to allow gas and suspended particulate matter (e.g., smoke) to be evacuated from the patient, both with and without an instrument inserted through the seal assembly. As shown, insufflation/evacuation gas 10 enters/exits a port 11 in seal assembly 1. Port 11 is in the seal assembly housing-through lower housing 5, as shown. Entering gas then flows, between an inner side wall of lower housing 5 and an outer side wall of backflow prevention seal 8 to pass through the cannula or through a gap between surgical instrument 3 and the cannula's inner wall into the patient. Evacuation gas follows a reverse path. Details of an example configuration to allow insufflation/evacuation gas to pass though seal assembly 1 are given below. Two or more ports 11 may optionally be used to ensure a clear path exists to allow gas to pass through the seal assembly In some embodiments, seal assembly 1 includes an instrument insertion guide 12 located on the proximal side of wiper seal 7. Instrument insertion guide 12 helps guide the distal end of a surgical instrument into wiper seal 7, for example so that the distal tip of instrument end effector 3a is urged away from puncturing, tearing, snagging on, or otherwise damaging wiper seal 7 as the instrument is inserted. As described in detail below, in some embodiments instrument guide 12 is fixed with reference to the seal assembly housing (e.g., it is optionally formed with upper housing 6 as a single piece), and in other embodiments instrument guide is formed as a separate piece from the seal assembly housing, and as a separate piece it may be fixed or it may move with reference to the seal assembly housing.

In one inventive aspect, the combination of seal assembly 1 and the surgical instrument inserted through seal assembly 1 are considered an assembly. In another aspect, the combination of seal assembly 1 and cannula 2 are considered an assembly. In yet another aspect, the combination of seal assembly 1, cannula 2, and the surgical instrument inserted through both seal assembly 1 and cannula 2 are considered an assembly. In two additional aspects, the combinations of seal assembly 1 and cannula 2, and of seal assembly 1, cannula 2, and the surgical instrument inserted through both seal assembly 1 and cannula 2, are expanded to include a teleoperated medical device that controls the surgical instrument movements. Teleoperated medical devices are known, such as the da Vinci Xi® Surgical System commercialized by Intuitive Surgical, Inc., Sunnyvale, Calif., and such medical devices are also referred to by terms such as "surgical system" or "surgical robot". As described above and below, the seal assembly is a component that allows the teleoperated medical device to carry out surgery by maintaining a proper gas-tight seal against a surgical instrument.

Figure 1A:
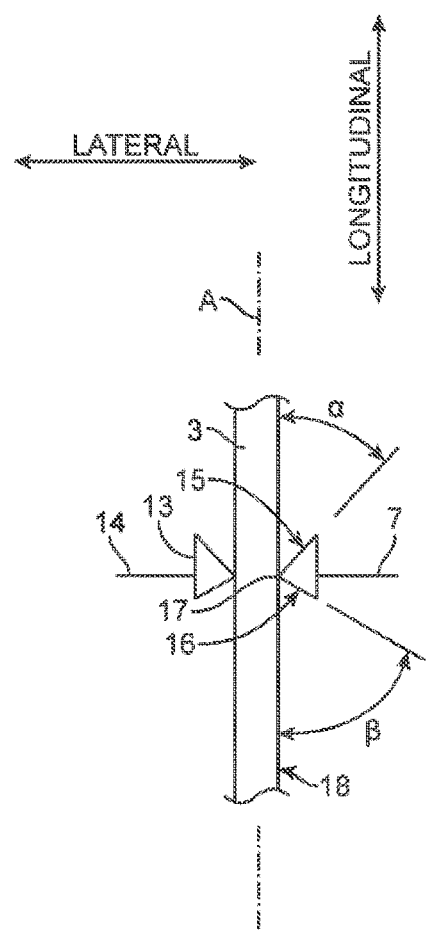
FIG. 1A is a diagrammatic, cross-sectional view of a portion of the seal assembly shown in FIG. 1.

FIG. 1A is a diagrammatic, cross-sectional view of a portion of seal assembly 1, similar to FIG. 1 but with several components omitted for clarity. Longitudinal and lateral directions are indicated by the labeled arrows, with longitudinal meaning a direction generally parallel to the instrument insertion and withdrawal axis, and lateral meaning a direction generally perpendicular to the instrument insertion and withdrawal axis. FIG. 1A shows surgical instrument 3's shaft inserted through wiper seal 7. Wiper seal 7 includes an inner sealing portion 13 and an outer flex portion 14 surrounding sealing portion 13. Flex portion 14 allows sealing portion 13 to move distally and proximally along the longitudinal axis A as surgical instrument 3 is inserted and withdrawn through wiper seal 7. Hex portion 14 also allows sealing portion 13 to move laterally (side-to-side) within the surgical instrument housing. Sealing portion 13 includes an upper annular face 15 and a lower annular face 16, which is reverse from upper face 15. Upper face 15 and lower face 16 intersect at annular wiper seal lip 17 to form a circular opening, and lip 17 seals against surgical instrument 3's shaft outer surface 18. Thus sealing portion 13 is relatively thick compared with flex portion 14 and so is more stiff than flex portion 14. But, sealing portion 13 is sufficiently laterally flexible so that it can accommodate various instrument shaft diameters. In one embodiment, for example, wiper seal 7 effectively seals against surgical instrument shaft diameters in the range of 4.7 to 9.4 mm (referred to as a 5-8 mm range). In another example embodiment, wiper seal 7 effectively seals against surgical instrument shaft diameters in the range of about 9.7 to 14.2 mm (referred to as a 10-12 mm range). The wiper seal may be sized to accommodate various other diameter ranges, or it may be made of a material that is best suited to work with a single specific instrument shaft diameter.

As shown, upper face 15 is angled at an angle α with reference to instrument 3's shaft, and lower face 16 is angled at an angle β with reference to instrument 3's shaft. Another way to describe this is that angles α and β are angled with reference to a longitudinal axis A defined between the seal assembly's top and bottom, so that a surgical instrument inserts and withdraws along longitudinal axis A. Angle α is smaller (more acute) than angle β. Accordingly, upper face 15's radial width is larger than lower face 16's radial width. As surgical instrument 3 inserts distally through wiper seal 7, contact between seal lip 17 and upper face 15 against shaft outer surface 18 tends to move sealing portion 13 distally. Likewise, as surgical instrument 3 withdraws through wiper seal 7, contact between seal lip 17 and lower face 16 against shaft outer surface 18 tends to move sealing portion 13 proximally.

The relatively thicker sealing portion 13, and the angles and/or radial widths of the upper face 15 and lower face 16, provide several advantages. A typical thin-membrane septum seal has a uniform or near-uniform thickness, and so is subject to puncture and tearing by the instrument tip when an instrument is inserted. Sealing portion 13's larger thickness with reference to flex portion 14 helps to guard against puncture or tearing as an instrument is first inserted, yet flex portion 14 provides an overall seal longitudinal and lateral flexibility similar to a thin septum seal's flexibility. As described below, in some configurations flex portion 14 provides superior flexibility characteristics for wiper seal 7 compared to a typical thin-membrane septum seal, since flex portion 14 can be made thinner because it is not contacted by the instrument. This overall flexibility accommodates longitudinal and lateral movements of the instrument shaft within the seal assembly during initial insertion, removal, and use. Upper face 15's relatively steep angle 2 helps to guide the instrument tip into the hole formed by seal lip 17, further reducing the risk of puncture or tearing. Seal portion 13's thickness that results from lip 17 being compressed against the instrument shaft to form a thicker contact with the instrument shaft, along with seal portion 13's increasing outward thickness, also helps to reduce or eliminate a problem of a portion of seal lip 17 being stretched into an oblong shape and separating from instrument shaft surface 18 if the shaft is moved laterally within the seal assembly, which breaks the seal by creating an opening between the lip 17 and surface 18. This situation is sometimes called a "cat-eye" condition due to the resulting seal opening shape, and it is more of a problem with instrument shaft diameters at the low end of a diameter range that a thin-membrane septum seal may accommodate. Because of sealing portion 13's generally triangular cross-sectional shape, with an apex at lip 17, the circular opening is easily expanded to accommodate various instrument shaft diameters, while the wiper seal function is preserved and sealing portion 13's longitudinal flexing is significantly reduced. The generally smaller amount of material near the circular opening allows sealing portion 13 to be laterally compressed outward with relatively lesser resistance, and the generally larger amount of material away from the circular opening tends to cause sealing portion 13 to increasingly resist lateral compression outward as the circular opening further expands.

It can be seen that due to upper face 15's relatively larger radial width compared with lower face 16's radial width, relatively more of upper face 15 will contact instrument shaft surface 18 compared with lower face 16 as the instrument inserts and withdraws. Stated another way, the contact area between upper face 15 and the instrument shaft is larger than the contact area between lower face 16 and the instrument shaft. This contact causes friction between wiper seal 7 and instrument shaft surface 18 that is relatively higher as the instrument is inserted and relatively lower as the instrument is withdrawn. The lower friction during instrument withdrawal helps prevent wiper seal 7 from being pulled proximally as the instrument is fully withdrawn, and so helps prevent the wiper seal from inverting proximally through the upper opening in the seal housing. In view of the illustrative wiper seal embodiments shown in the drawings and described below, persons of skill in the art will understand that even if angles α and β are equal, or even if angle α is larger than angle β, sealing portion 13 optionally may be configured so that upper face 15's radial width (i.e., contact area) is larger than lower face 16's radial width in order to provide the relatively higher instrument insertion friction. Persons of skill in the art will understand that providing good sealing function with low friction (e.g., low enough to avoid a stick-slip condition) may be desirable, especially in teleoperated applications in which smooth control is desired as the instrument shaft constantly moves back and forth through the seal. But, such persons will also understand that providing a reasonable resistance to instrument insertion is desirable so that an instrument cannot inadvertently slip through the seal and injure the patient (e.g., due to the instrument's own weight during a manual laparoscopic procedure). The described sealing portion of the wiper seal offers such an increased insertion resistance friction, as well as acceptable insertion/withdrawal friction. Additional asymmetric insertion/withdrawal resistance features, as well as other wiper seal 7 features, are described in detail below.

As shown in FIG. 1A, flex portion 14 is attached to an outer perimeter of sealing portion 13 longitudinally midway between upper face 15 and lower face 16. Also, flex portion 14 is shown as being longitudinally aligned with lip 17. Optionally, however, flex portion 14 is attached to sealing portion 13's perimeter at various longitudinal positions, including extreme proximal and distal positions. Likewise, flex portion 14 is optionally positioned with various longitudinal relations with lip 17. Examples of such longitudinal attachment and lip alignments are shown in detail below.

First Example

Figure 2:
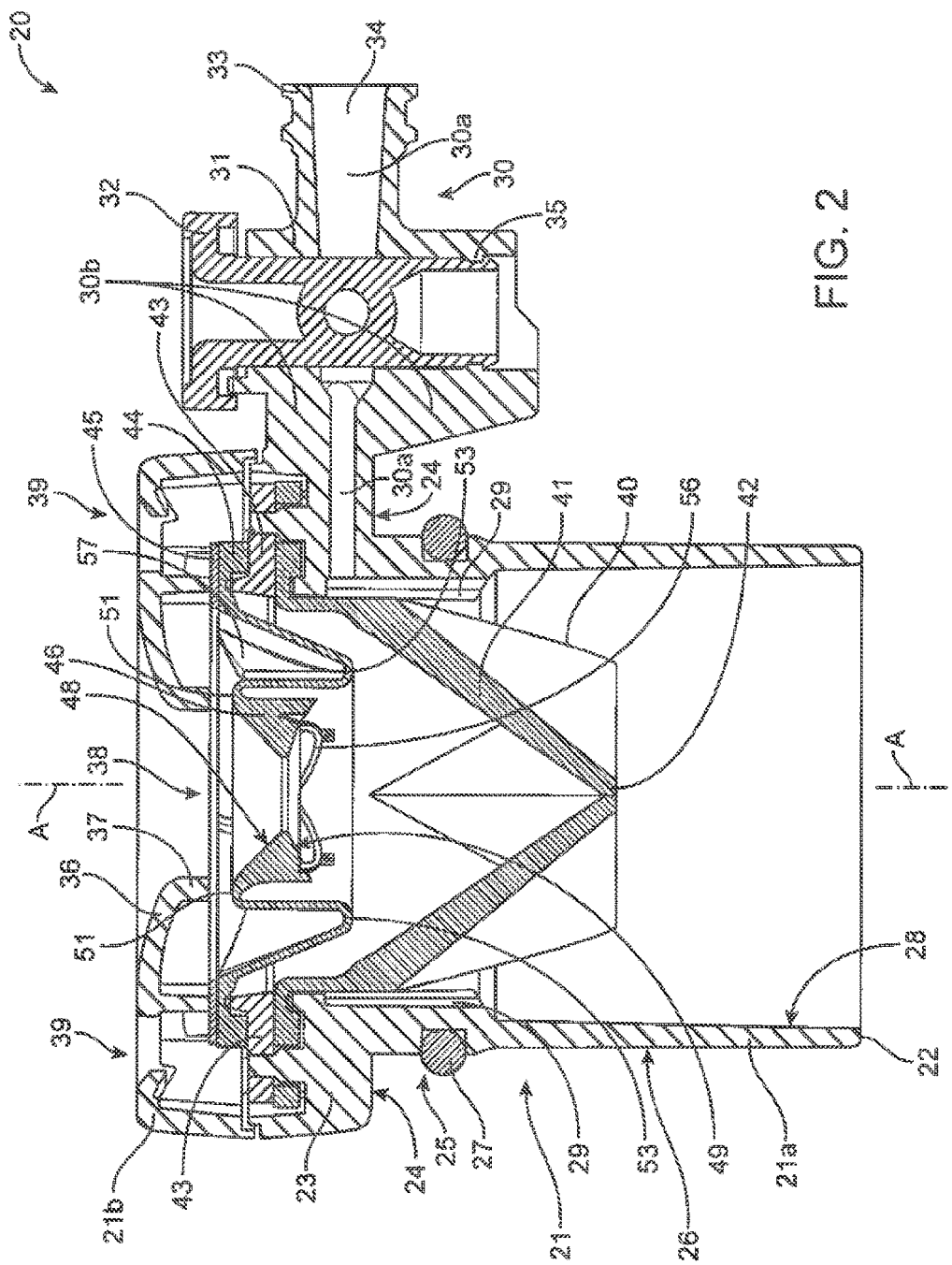
FIG. 2 is a cross-sectional elevation view of an example surgical instrument seal assembly.

FIG. 2 is a cross-sectional elevation view of an illustrative surgical instrument seal assembly 20. Seal assembly 20 includes a lower housing 21a and an upper housing 21b that when assembled together form a generally cylindrical seal assembly housing 21. As shown, during manufacturing lower housing 21a and upper housing 21b are first aligned with hex holes and interference pins, and then ultrasonic welding is used to secure lower and upper housings 21a,21b together. Other well-known permanent joining techniques may be used, such as permanent press fitting or use of adhesives. In one embodiment, the upper and lower housing pieces 21a,21b are made of rigid polycarbonate, and optionally other rigid materials such as plastic or metal may be used.

Lower housing 21a includes a distal end 22, which is inserted into a cannula bowl at the proximal end of a surgical cannula (not shown), and a proximal end 23, which remains outside the cannula. Proximal end 23 is optionally generally larger than distal end 22, and a relief surface 24 under proximal end 23 rests on and is held against the proximal end of the cannula. Lower housing 21a further includes an annular groove 25 in its outer wall surface 26. An O-ring 27 is inserted into groove 25, and when seal assembly 20 is inserted into the cannula bowl, O-ring 27 seals against the cannula bowl's inner wall surface to prevent insufflation gas from escaping between the cannula bowl's inner side wall and lower housing 21a's outer side wall. O-ring 27 also allows the seal assembly to rotate within the cannula bowl while maintaining the seal between the seal assembly and cannula bowl, as discussed in more detail below. Persons of skill will understand that O-ring 27 is representative of various packing- or gasket-type seals that may be generally termed cannula seals and function to seal between the seal assembly's outer sidewall and the cannula bowl's inner sidewall, in some implementations allowing the seal assembly to rotate within the cannula bowl while maintaining the seal.

Figure 7:
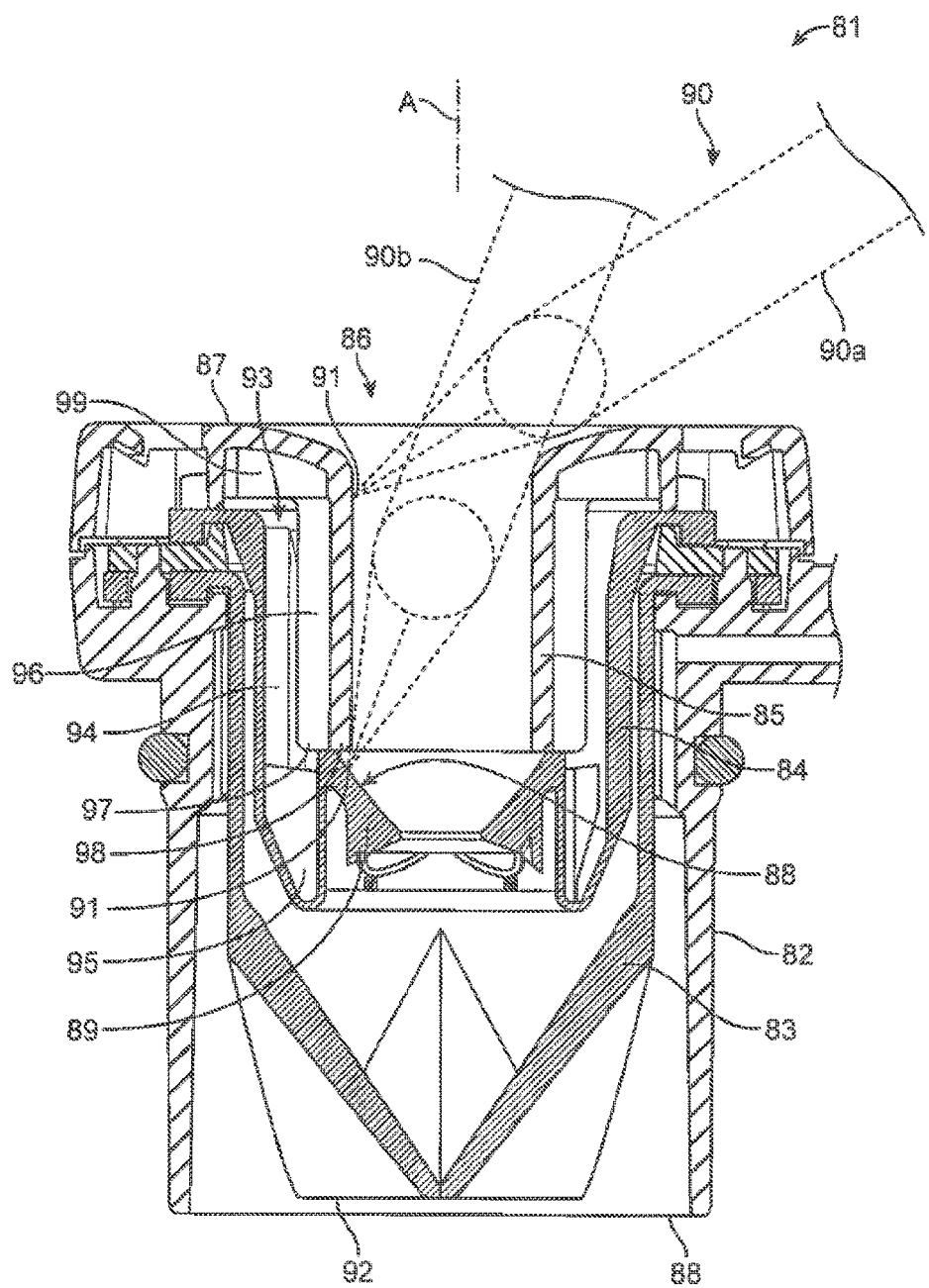
FIG. 7 is a cross-sectional elevation view of a portion of another example seal assembly embodiment.

Lower housing 21a further includes an inner wall surface 28, which tapers slightly laterally outward toward distal end 22 to allow increased lateral movement of the backflow prevention seal (see also e.g., FIG. 7 in which an extended backflow prevention seal is shown). As shown in FIG. 2, inner wall surface 28 is optionally slightly necked down near upper housing portion 21b. The necking-down increases structural strength in the lower housing portion. Also as shown in FIG. 2, several optional radially inward projecting ribs 29 are in this necked down region. The ribs 29 help prevent the backflow seal's outer side wall surface from blocking gas flow as the gas passes between the housing's inner side wall and the backflow seal's outer surface side wall to enter or exit the surgical site via a port in the seal assembly.

As shown in FIG. 2, lower housing 21a also includes an optional gas valve 30, which includes a valve body 31, a rotating valve member 32, an external fitting 33 (e.g., a threaded Luer-Lock as shown), an internal fitting 34 (e.g., a Luer taper fitting as shown), and a gas channel 30a. As shown, valve member 32 is snap-fit into and rotationally secured in valve body 31 by using annular retainer flange 35. In some embodiments one or more optional support ribs 30b are placed between the valve body 31 and the seal assembly housing 21 to provide additional structural strength to help prevent valve 30 from breaking away from housing 21. As shown, the lower housing 21a, valve body 31, external fitting 33, and support ribs 30b are formed as an integral single piece, and optionally they may be formed as two or more pieces that are joined together. During a surgical procedure, an insufflation gas supply (not shown) may be coupled to fitting 33,34, and valve member 32 is rotated to allow gas to flow inward into the seal assembly through channel 30a. Alternatively, an evacuation gas sink (not shown; e.g., a vacuum source) may be coupled to fitting 33,34, and valve member 32 is rotated to allow gas to flow outward from the seal assembly through channel 30a.

Upper housing 21b includes an optional distally tapering annular funnel portion 36, which leads to an optional annular instrument insertion guide 37 that extends distally toward the underlying wiper seal. The funnel portion 36 and instrument insertion guide 37 together define a circular hole 38 in upper housing 21b, centered on the seal assembly's longitudinal centerline, through which an instrument is inserted. Hole 38's diameter is larger than the hole in the underlying wiper seal, and the relation between hole 38's diameter and the dimensions of the wiper seal's upper face surface is discussed in detail below. Funnel portion 36 helps guide a surgical instrument tip toward hole 38, and instrument guide 37 helps align and guide the instrument tip for insertion through the underlying wiper seal.

Upper housing 21b optionally includes one or more latch receiving features 39 that allow an object to be removably coupled to housing 21. As shown, latch receiving features 39 are windows that allow obturator latches (not shown) to extend through and engage upper housing 21b's inner surface to hold an obturator (not shown) fully inserted in the seal (see FIG. 15 and associated text, below). The obturator latches engage under the perimeter that defines the window. The cannula, seal, and obturator together form an assembly that allows a surgeon to insert the cannula through the patient's body wall. It should be understood that latch receiving features 39 as shown are representative of many well-known latch mechanisms that will allow an obturator or other object to be removably coupled to the top of housing 21. In another example, latches on a second seal assembly (not shown) hold the second seal assembly against the top of housing 21. See e.g., U.S. Pat. No. 6,123,689 (showing a "reducer" seal that can be removably coupled to the top of a main seal assembly). The second seal assembly includes a wiper seal hole with a smaller diameter than the diameter of the hole of the wiper seal in housing 21. The second seal assembly when coupled to housing 21 forms additional various combinations similar to combinations described elsewhere in this document.

As shown in FIG. 2, a backflow prevention seal 40 is sandwiched between lower housing 21a and upper housing 21b. As depicted in this embodiment, backflow prevention seal 40 is a cross-slit seal. The thickness of each of backflow prevention seal 40's folded sidewalls 41 tapers slightly toward seal 40's distal end 42. The thicker folded side walls 41 at seal 40's proximal end help the backflow prevention seal to snap back to the closed position when an instrument is removed. The thinner folded side walls 41 at seal 40's distal end provide increased side wall flexibility and resulting lower friction between seal 40 and an instrument when the instrument is inserted through seal 40. The relatively thinner distal side walls 41 also help fluid backpressure against the side walls' outer surfaces keep the seal closed when an instrument is removed. Backflow prevention seal 40 is oriented within lower housing 21a so that one of the sidewall 41 inward folds is aligned with gas channel 34 (i.e., the adjacent sidewall 41 outward folds are offset 45 degrees from gas channel 34, as shown), in order to ensure sufficient gas flow past the folded sidewalls 41, which are pushed against ribs 29 when an instrument is inserted through backflow prevention seal 40. The interior of backflow prevention seal 40 is made longitudinally deep enough and laterally wide enough so that backflow prevention seal 40 does not interfere with movement of the overlying wiper seal as the wiper seal moves longitudinally and laterally. In an example embodiment, backflow prevention seal 40 is made of a medical grade elastomeric material, such as chlorinated polyisoprene or other rubber material, such as silicone, urethane, etc. Other suitable materials may be used.

FIG. 2 shows an optional annular spacer 43 positioned over backflow prevention seal 40 and sandwiched between lower and upper housing portions 21a,21b. As described in more detail below, in some embodiments annular spacer 43 is combined as an integrally formed single piece with a latch that removably secures the housing 21 to a cannula. In some embodiments, spacer 43 is positioned over both the wiper and backflow prevention seals, so that the outer perimeters of the wiper and backflow prevention seals touch. As depicted, however, spacer 43 is positioned between the wiper and backflow prevention seals, which provides more longitudinal space between the wiper seal and the backflow seal's proximal end, and so allows the wiper seal to properly operate without contact interference from the backflow prevention seal. Spacer 43 may optionally include one or more annular bosses that compress either or both the backflow prevention seal and the wiper seal when the upper and lower housing pieces are secured together in order to ensure a gas-tight seal between each seal and the housing, and in order to prevent each seal from rotating within the housing.

As depicted, wiper seal 44 is positioned over annular spacer 43 so that wiper seal overlies (is proximal of) backflow prevention seal 40. The instrument hole in wiper seal 44 is aligned over the intersection of the cross slits in backflow prevention seal 40, so that an instrument passes through the centers of both the wiper and backflow prevention seals. Details of the wiper seal are discussed in more detail below.

As depicted, an optional annular spacer 45 is positioned over (proximal of) wiper seal 44's outer perimeter. When used, annular spacer 45 helps distribute the pressure of upper housing 21b against wiper seal 44. In addition, annular spacer 45 may optionally include a wiper seal anti-inversion feature, described in more detail below.

Thus, FIG. 2 shows wiper seal 44 positioned over backflow prevention seal 40 in seal housing 21, sandwiched along with optional spacers 43 and 45 between lower housing 21a and upper housing 21b.

Wiper Seal

Figure 3:
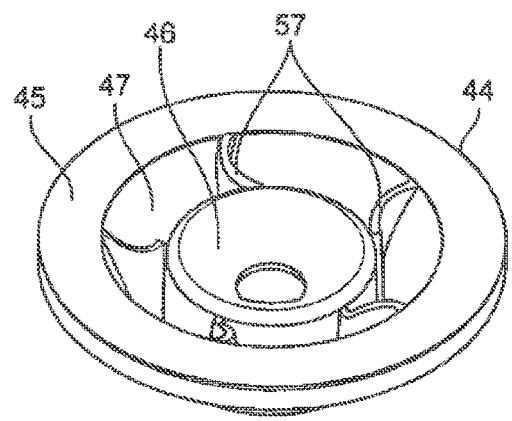
FIG. 3 is an upper perspective view of an example wiper seal embodiment.
Figure 3A:
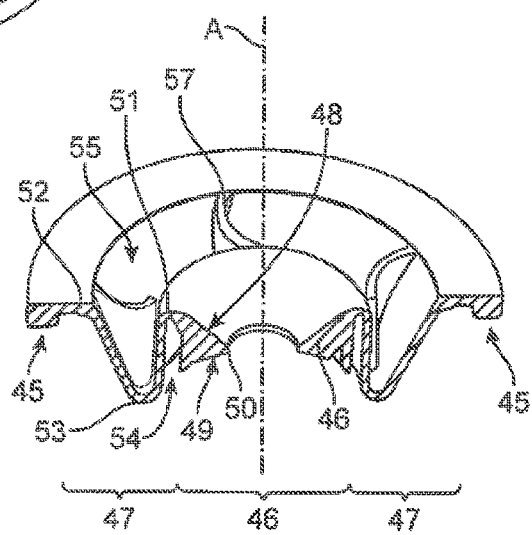
FIG. 3A is a cross-sectional upper perspective view of the wiper seal embodiment shown in FIG. 3.
Figure 3B:
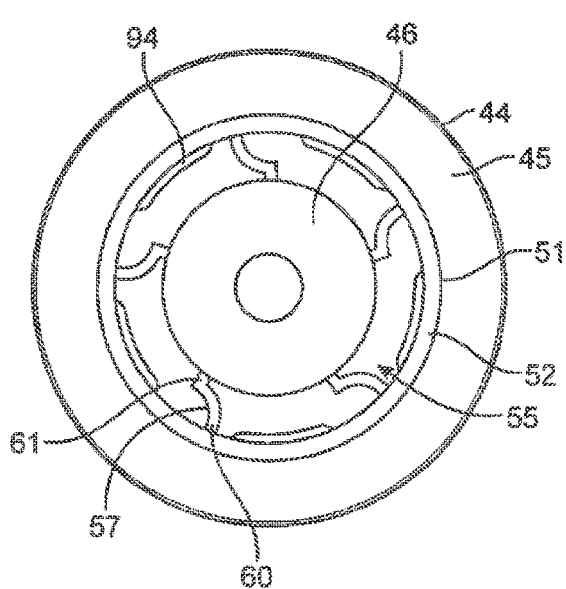
FIG. 3B is a top plan view of the wiper seal embodiment shown in FIG. 3.
Figure 4:
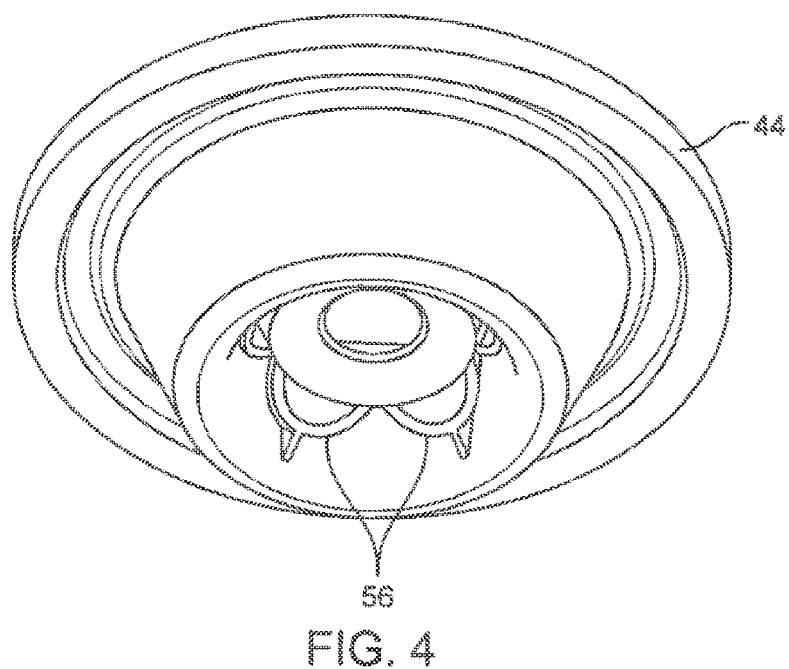
FIG. 4 is a lower perspective view of the wiper seal embodiment shown in FIG. 3.
Figure 4A:
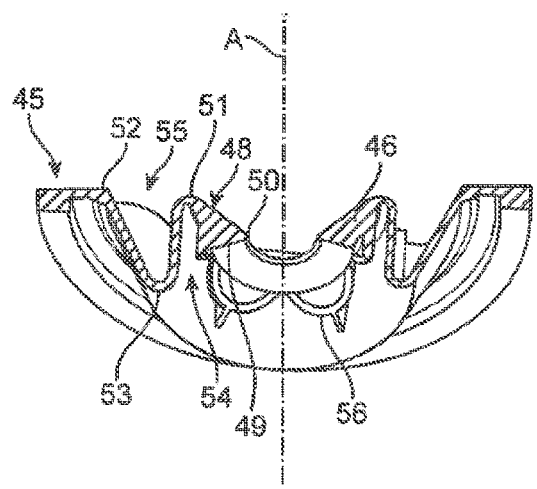
FIG. 4A is a cross-sectional lower perspective view of the seal embodiment shown in FIG. 3.
Figure 4B:
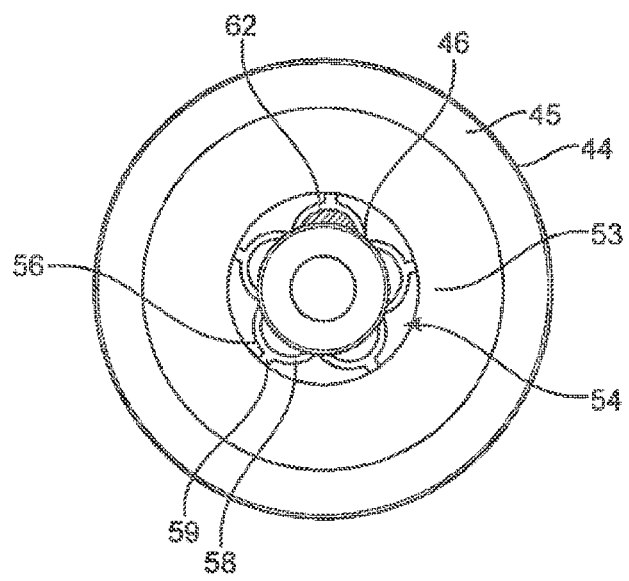
FIG. 4B is a bottom plan view of the embodiment shown in FIG. 3.

FIG. 3 is an upper perspective view of an example wiper seal embodiment, FIG. 3A is a cross-sectional upper perspective view of the wiper seal embodiment shown in FIG. 3, and FIG. 3B is a top plan view of the wiper seal embodiment shown in FIG. 3. FIG. 4 is a lower perspective view of the wiper seal embodiment shown in FIG. 3, FIG. 4A is a cross-sectional lower perspective view of the seal embodiment shown in FIG. 3, and FIG. 4B is a bottom plan view of the embodiment shown in FIG. 3. To avoid prolix description, the various features described with reference to this wiper seal embodiment, as well as the wiper seal features described above, apply to other wiper seal embodiments described above and below.

Referring to FIGS. 2, 3, 3A, 3B, 4, 4A, and 4B, wiper seal 44 is generally annular and includes an annular outer perimeter portion 45, an annular inner sealing portion 46, and an annular flex portion 47 between perimeter portion 45 and sealing portion 46. Perimeter portion 45 supports wiper seal 44 within housing 21, so that sealing portion 46 can move longitudinally and laterally as an instrument shaft passing through wiper seal 44 moves inside housing 21. As depicted, perimeter portion 46 has an optional small annular boss on its distal side, and various other optional configurations (e.g., annular boss on the proximal side, interrupted annular bosses or projections, etc.) may be used for mounting wiper seal 44 within the seal assembly housing. Sealing portion 46 functions as generally described with reference to FIGS. 1 and 1A. It includes an annular upper face 48 and an annular lower face 49 that meet at circular seal lip 50, which defines a hole through which a surgical instrument shaft is inserted and withdrawn. Seal lip 50 seals against the surgical instrument shaft's outer surface. Seal lip 50 may be formed as a single, rounded surface, or optionally it may be formed as other surface shapes, such as flat, corrugated, etc. Optionally, one or more small, discrete annular rings are placed on lip 50 for sealing against the instrument shaft. Sealing portion 46 is flexible, and so it accommodates various instrument shaft diameters (e.g., about 5-8.5 mm or about 10-12 mm)—the sealing portion 46 dimensions can be varied to suitably accommodate other diameter ranges). It can be seen that upper face 48's radial width is larger than lower face 49's radial width, and the angle between upper face 48 and an inserted instrument shaft is more acute than an angle between lower face 49 and the inserted instrument shaft.

Flex portion 47 surrounds sealing portion 46, and it (i) allows sealing portion 46 to move distally and proximally (longitudinally) within the seal assembly, (ii) allows sealing portion 46 to move from side-to-side (laterally) within the seal assembly without significant distortion (thus reducing the "cat-eye" problem described above), and (iii) accommodates sealing portion 46 stretching radially outward when a large diameter instrument shaft is inserted. Thus the benefits of the various aspects of sealing portion 46 are combined with the benefits of flex portion 47. As shown, flex portion 47 has a general annular folded bellows configuration, which is alternately described as an annular corrugation configuration, that includes one or more upper (proximally oriented) annular folds and/or one or more lower (distally oriented) annular folds, with annular grooves separating adjacent upper folds and adjacent lower folds (i.e., a groove is formed by the reverse of the fold). The folds act as hinges, although the flex portion 47 material between the folds may also stretch. In other embodiments, other suitable flex portion 47 configurations may be used, including for example flat (planar), annular diaphragms having constant or varying thickness.

In the depicted embodiment, flex portion 47 joins to sealing portion 46 at an inner upper annular fold 51 and joins to perimeter portion 45 at an outer upper annular fold 52. There is a lower annular fold 53 between the upper annular folds 51 and 52. As a result, a lower annular groove 54 is formed between sealing portion 46 and lower annular fold 53, and an upper annular groove 55 is formed between the upper annular folds 51 and 52. Support ribs 56 are positioned in lower annular groove 54, and support ribs 57 are positioned in upper annular groove 55. As shown, there are five each of support ribs 56 and 57, and other numbers (e.g., three, four, six, or more) may be used. Individual support ribs 56 and 57 are generally positioned opposite one another on the obverse and reverse of wiper seal 44, although they may be optionally placed at other mutually relative orientations. In addition, in some implementations the number of support ribs 56 may be different from the number of support ribs 57. And, support ribs 56 and support ribs 57 may optionally be symmetrically or asymmetrically spaced within an annular groove. Symmetrical spacing of three or more support ribs tends to keep resistance to motion constant in all lateral directions, and asymmetrical spacing (or the use of only two support ribs oriented opposite one another) tends to favor motion in one or more lateral directions.

As shown in FIGS. 4, 4A, and 4B, support ribs 56 are equally spaced in lower annular groove 54. Each support rib 56 has two portions—a truncated semi-circular cylinder portion 58 that is joined at both sides to sealing portion 46, and a web portion 59 that extends between the semi-cylinder portion 58 and lower annular groove 54's outer sidewall. The semi-cylinder portions 58 of support ribs 56 are generally arranged to form a scalloped pattern around sealing portion 46. As depicted, the semi-cylinder portions 58 are slightly separated from one another at sealing portion 46, and they may optionally touch one another at sealing portion 46.

Referring to FIGS. 3, 3A, and 3B, support ribs 57 are equally spaced in upper annular groove 55. Each support rib 57 has two portions-a truncated quarter-circle cylinder portion 60 that is joined at one side to upper annular groove 55's outer sidewall, and a web portion 61 that extends between portion 60's other side and upper annular groove's inner sidewall. It can be seen that support rib 57's shape is similar to support rib 56's shape, except that support rib 57 has only about one-half of support rib 56's semi-cylindrical portion.

Both support ribs 56 and support ribs 57 may have other shapes. For example, support ribs 57 may have a semi-cylinder portion, or support ribs 56 may have a quarter-cylinder portion. Other support rib shapes include a single, smooth (e.g., S-shaped) or sharply-angled (e.g., zig-zag) folded piece between groove sidewalls. The tops of support ribs 57 and the bottoms of support ribs 57 may be truncated as shown as described, or may be generally parallel to seal 44's lateral orientation.

It can be seen from FIGS. 2, 4, 4A, and 4B that support rib 56's attachment to lower annular groove 54's outer sidewall extends below (distal) the level of sealing portion 46. This configuration acts as an anti-inversion feature to help prevent sealing portion 46 from being pulled proximally during instrument withdrawal and unfolding upper annular fold 51 (i.e., inverting the seal). The support rib 56 configuration provides relatively small resistance to compression and relatively large resistance to extension. Therefore, the semi-cylinder portions 58 of support ribs 56 allow sealing portion 46 to stretch open to accommodate larger diameter instrument shaft diameters, which symmetrically compresses lower annular groove 54. The semi-circular portions 58 also allow lower annular groove 54 to be asymmetrically compressed as sealing portion 46 moves laterally within flex portion 47.

Thus both anti-inversion benefits and low resistance to compressing the annular groove are provided. The semi-cylindrical shape enables the support rib 56 to extend a relatively short distance with a relatively low resistance as the semi-cylinder's walls are pulled to straighten into a V-shape, and thereafter provide a relatively high resistance to further extension, which requires the support rib material itself to stretch. The semi-cylinder shape also enables the support rib 56 to almost fully collapse upon itself with little resistance. Artisans will understand, too, that the semi-cylinder shape's vertical walls allow for easy molding, so that the full wiper seal can be formed as a single, uniform piece. It can be seen that similar features and advantages exist in other support rib 56 configurations described above and below, as well as in the support rib 57 configurations as described below.

Further, although a specific embodiment has been described, many variations are possible, such as reversing the web and semi-cylinder orientation so that the web is closer to the sealing portion (depending on the groove configuration), altering the semi-cylindrical shape to include other curved or straight sides, etc. Therefore, in general terms the depicted support rib 56 can be described as having two walls, the first side of each wall being anchored to one of groove 54's sidewalls, and the second side of each wall being joined together and anchored to the other one of groove 54's sidewalls. And further, the level at which support rib 56's walls join groove 54's outer sidewall extends below (distal of) the level at which support rib 56's walls join groove 54's inner sidewall. Still further, although groove 54's inner sidewall is depicted as being defined by sealing portion 46, support ribs 56 may optionally be placed in any groove in flex portion 47.

In some wiper seal 46 embodiments, a lubricant 62, such as a medical grade silicone lubricant, is placed in one or more of the pockets formed between a support rib 56's semi-cylindrical portion 58 and sealing portion 46. As a surgical instrument is inserted and withdrawn through sealing portion 46, sealing portion 46's and flex portion 47's flexing causes some lubricant 62 to be pushed out of the pocket, and it then migrates across lower face 49 to lubricate the contact between the surgical instrument shaft and sealing portion 46. One suitable lubricant is NuSil Technology LLC's MED-420 (at ~5,000 cP). Another suitable lubricant is NuSil's MED-361 (at ~12,5000 cP), and other suitable lubricants with various viscosities may be used.

Referring now to FIGS. 2, 3, 3A, and 3B, it can be seen that due to upper annular groove 55's sidewall angles with reference to a longitudinal axis, the support rib 57 orientations in upper annular groove 55 are generally reversed from the support rib 56 orientations in lower annular groove 54. The level at which each support rib 57 attaches to upper annular groove 55's outer sidewall extends above (proximal of) the level at which each support rib 57 attaches to upper annular groove 55's inner sidewall (the top of which being where the flex portion 47 joins the sealing portion 46). This configuration helps prevent sealing portion 46 from being pushed distally and possibly unfolding lower annular fold 53 during instrument insertion. Support rib 57's quarter-cylindrical portion 60 and web 61 combination functions similarly to support rib 56's semi-cylindrical portion 58 and web 59 combination, and similar configuration variations as described above are possible. It can be seen that each support rib 57 is somewhat larger than each support rib 56. The quarter-cylindrical portion 60 functions to further reduce resistance to collapse compared with semi-cylindrical portion 58, so that upper annular groove 55 easily collapses symmetrically as sealing portion 46 expands to accommodate a relatively larger instrument shaft diameter, and groove 55 easily collapses asymmetrically as sealing portion 46 moves laterally. In some embodiments, however, support rib 57 includes a semi-cylindrical portion (or variations) similar to support rib 56. And, as for support ribs 56 in multiple lower annular grooves, if flex portion 47 includes multiple upper annular grooves, then support ribs 57 may be placed in any number of the upper annular grooves.

Figure 3C:
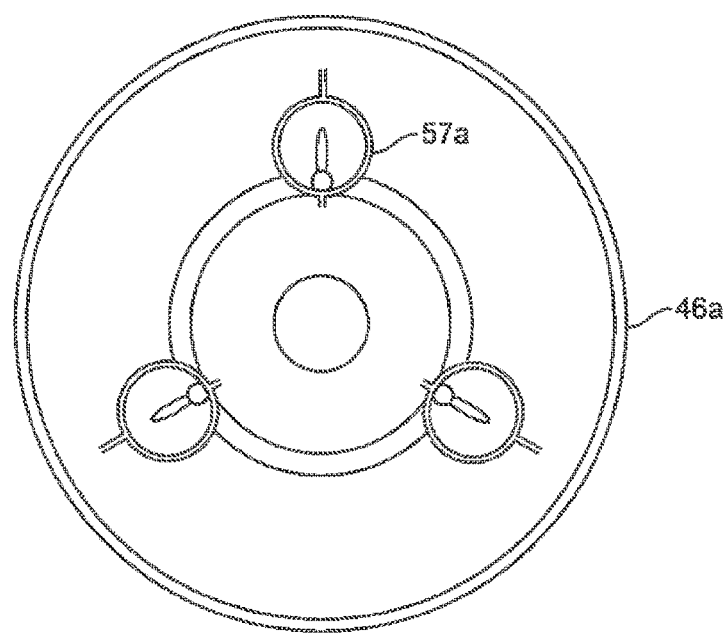
Figure 3D:
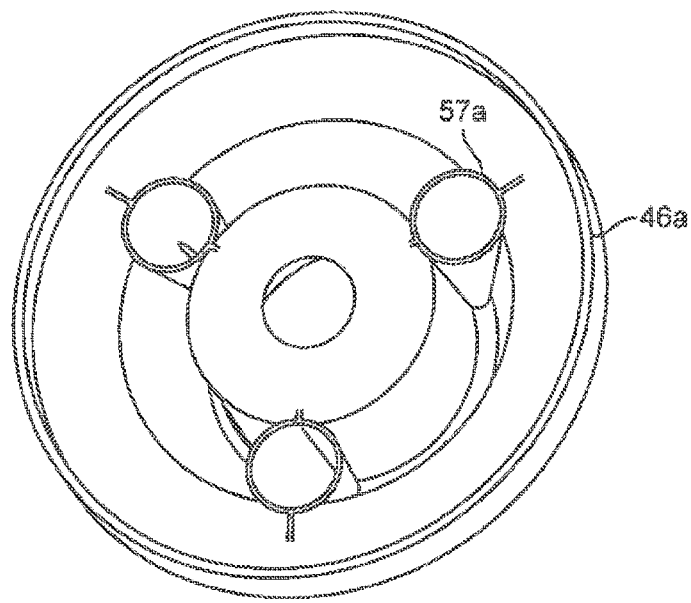

As referred to above, various other support rib configurations may be used in either the upper or lower grooves formed by the annular folds in the wiper seal's flex portion. FIG. 3C and FIG. 3D are top and perspective views of a wiper seal 46*a*, in which equally-spaced support ribs 57*a* are positioned in a flex portion groove. Support ribs 57*a* each include a truncated cone section oriented in a longitudinal direction with the apex toward the bottom of the groove, and with the conic section walls coupled by small web portions to the groove's inner and outer sidewalls. The truncated cone is optionally right or oblique as shown, optionally circular as shown or other shape.

Figure 3E:
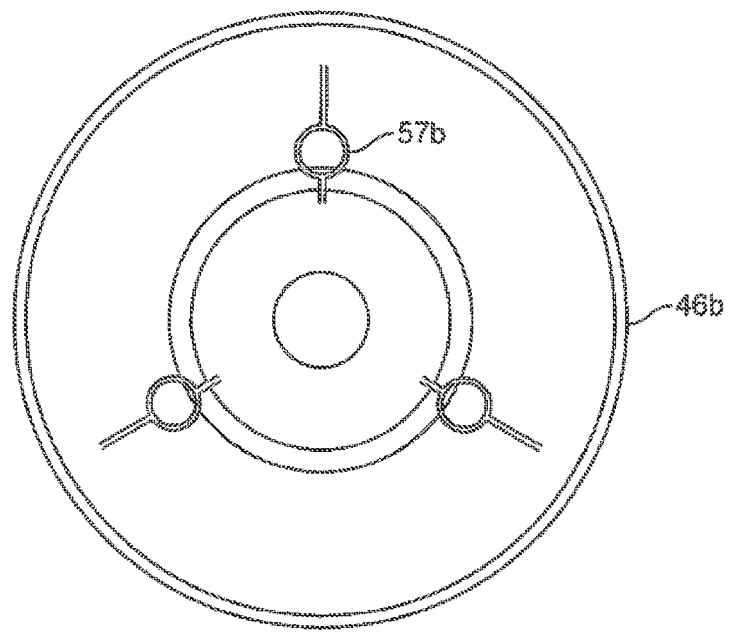
Figure 3F:
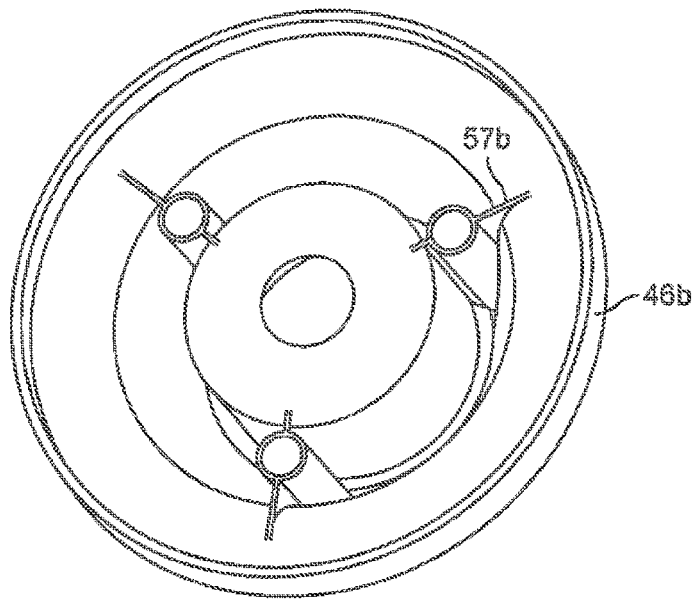

FIG. 3E and FIG. 3F are top and perspective views of a wiper seal 46*b*, in which equally-spaced support ribs 57*b* are positioned in a flex portion groove. Support ribs 57*b* each include a cylinder oriented in a longitudinal direction in the groove, and the cylinder walls are coupled by small web portions to the groove's inner and outer sidewalls. The diameters of the cylinders in support ribs 57*b* are somewhat less than the groove's width at the top of the groove.

Figure 3G:
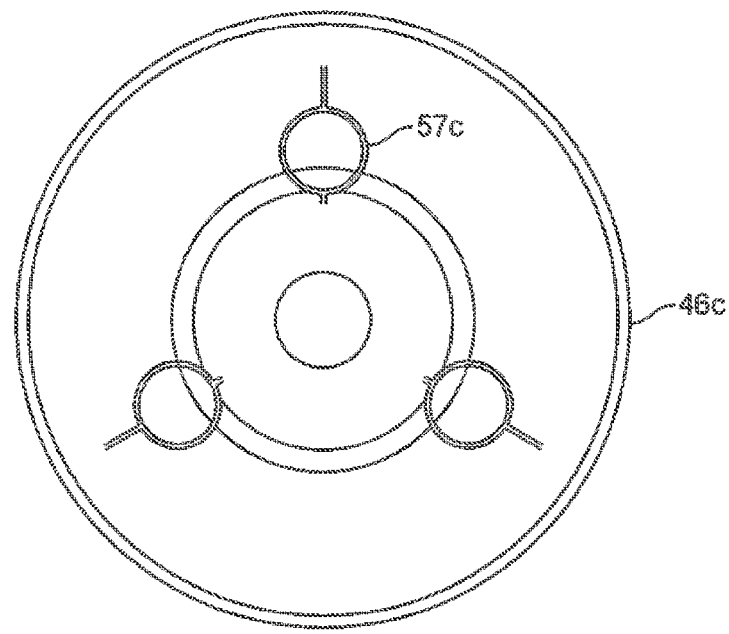
Figure 3H:
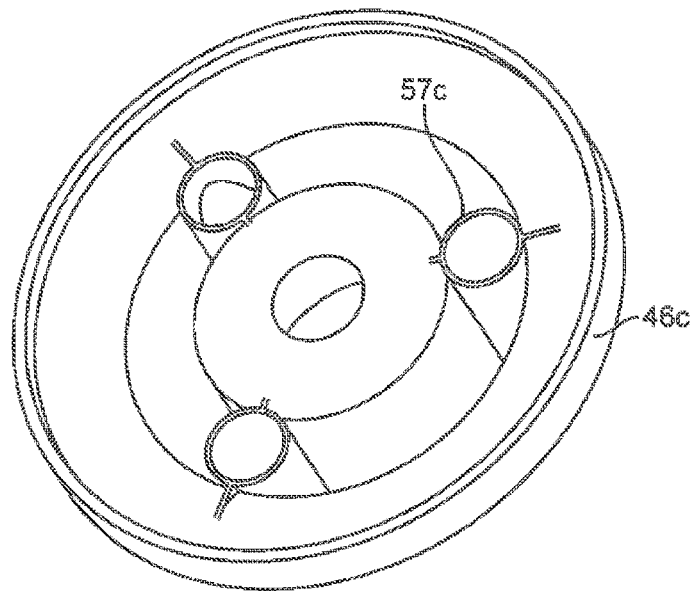

FIG. 3G and FIG. 3H are top and perspective views of a wiper seal 46*c*, in which equally-spaced support ribs 57*c* are positioned in such a groove. Similar to support ribs 57*b*, support ribs 57*c* each include a cylinder oriented in a longitudinal direction in the groove, and the cylinder walls are coupled by small web portions to the groove's inner and outer sidewalls. The diameter of the cylinders in support ribs 57*c* are larger than the diameters of the cylinders in support ribs 57*b*, the diameters being about the groove's width at the top of the groove.

Figure 3I:
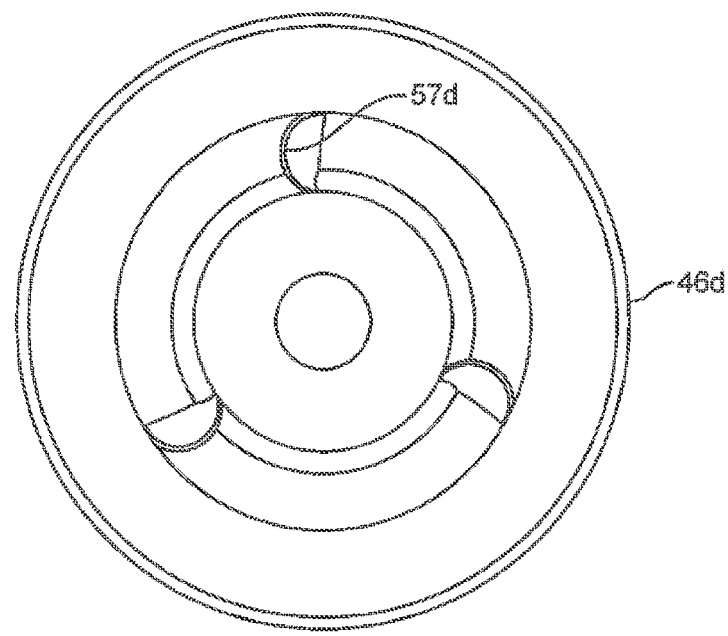
Figure 3J:
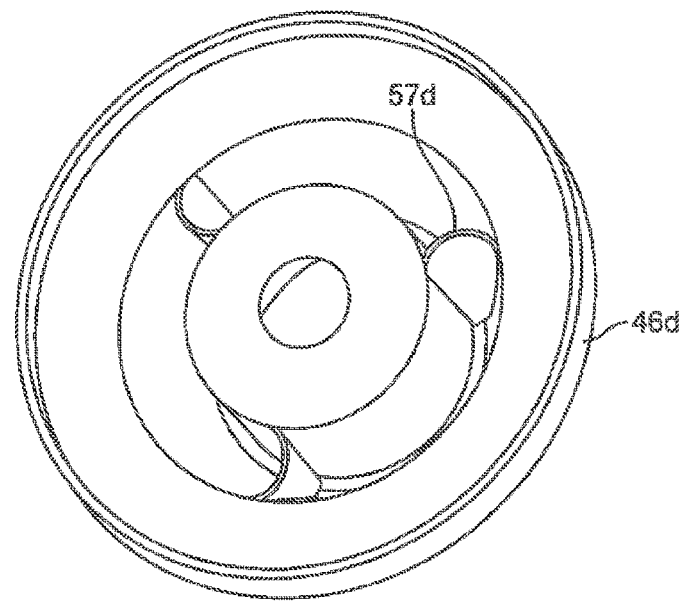

FIG. 3I and FIG. 3J are top and perspective views of a wiper seal 46*d*, in which equally spaced support ribs 57*d* are positioned in a flex portion groove. In contrast to support ribs 57*a* (FIGS. 3C and 3D), support ribs 57*d* are truncated semi-cone sections, with one side edge of the cone section being coupled to the groove's inner sidewall, and the other side edge of the cone section being coupled to the groove's outer sidewall.

Figure 3K:
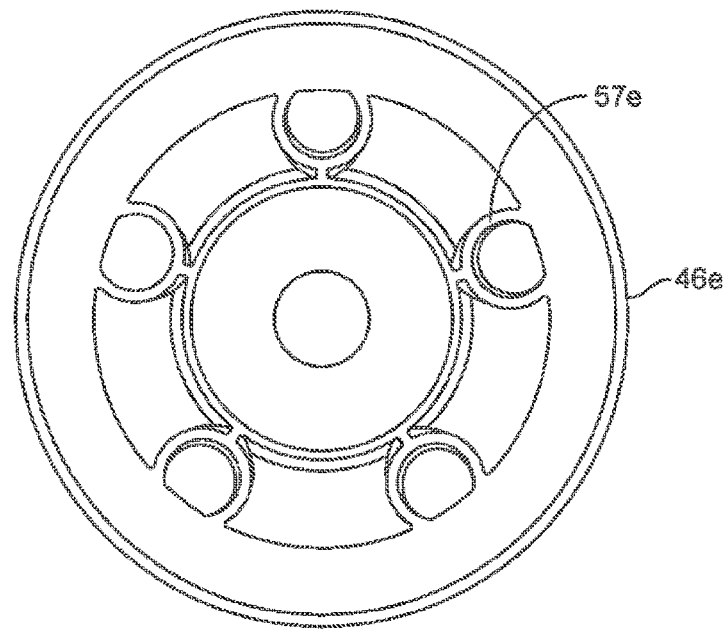
Figure 3L:
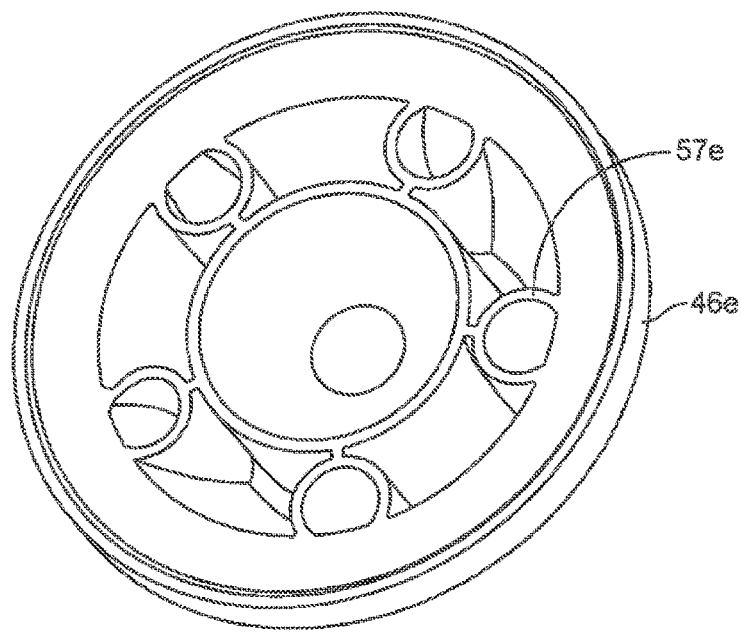

FIG. 3K and FIG. 3L are top and perspective views of a wiper seal 46*e*, in which equally-spaced support ribs 57*e* are positioned in a flex portion groove. The configuration of each support rib 57*e* is similar to the configuration of support ribs 56 (FIGS. 4, 4A, and 4B), except FIGS. 3K and 3L illustrate that the truncated semi-cylindrical configuration may be positioned in a top groove, and that the truncated semi-cylinders may be oriented with their openings radially outward.

Figure 3M:
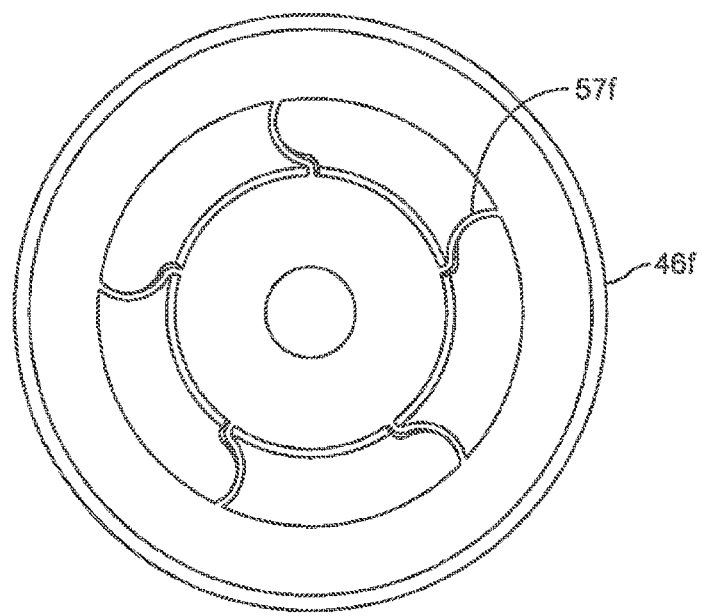
Figure 3N:
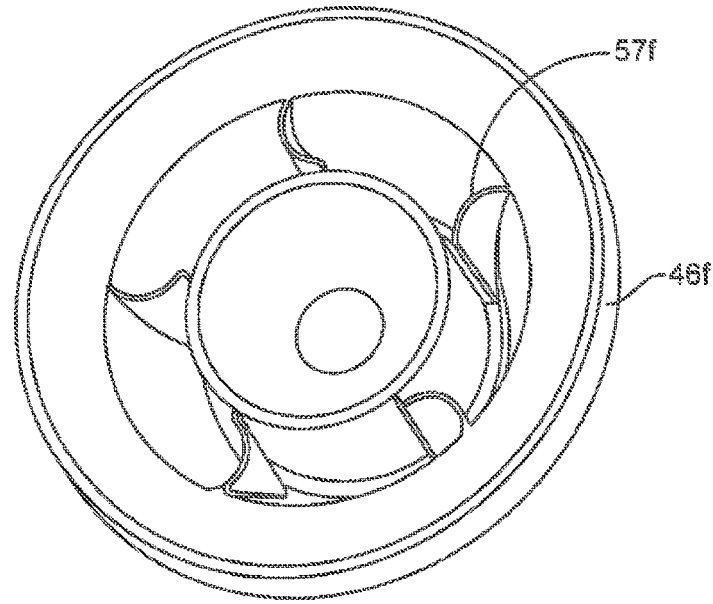

FIG. 3M and FIG. 3N are top and perspective views of a wiper seal 46*f*, in which equally-spaced support ribs 57*f* are positioned in a flex portion upper groove. The configuration of each support rib 57*f* is similar to the configuration of support ribs 57 (FIGS. 3, 3A, and 3B).

Figure 3O:
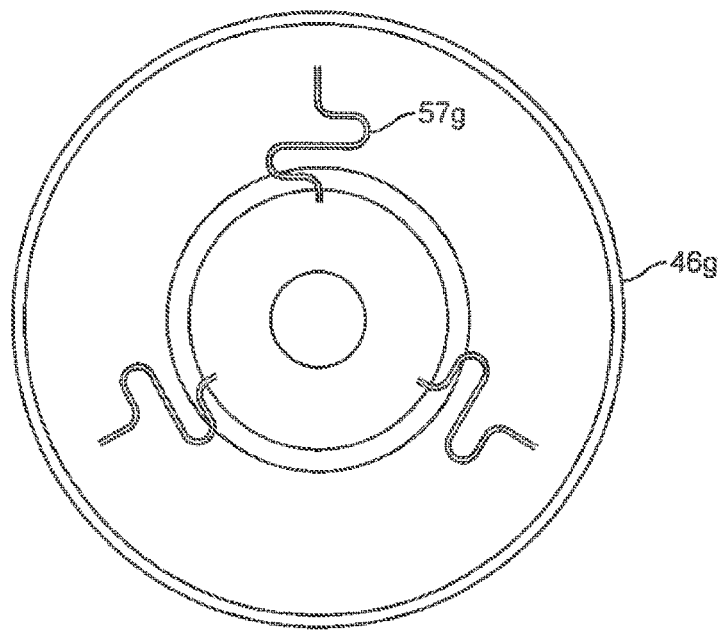
Figure 3P:
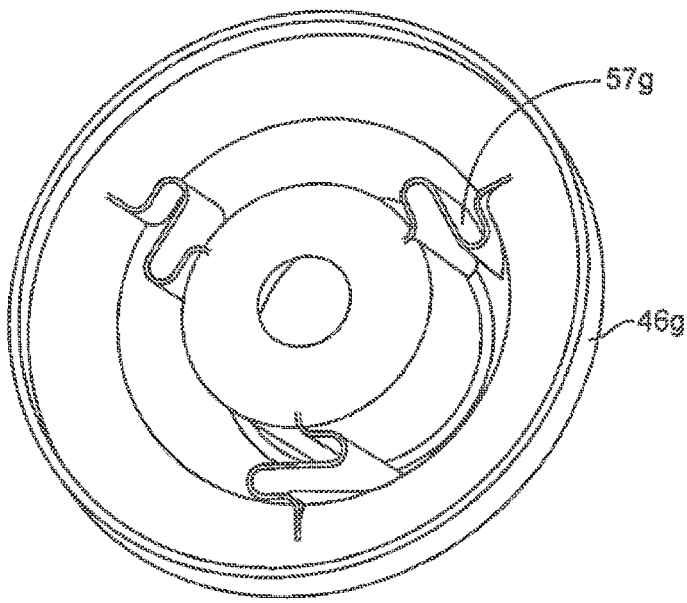

FIG. 3O and FIG. 3P are top and perspective views of a wiper seal 46*g*, in which equally-spaced support ribs 57*g* are each positioned in a flex portion groove. The configuration of each support rib 57*g* is a serpentine S-curve, with one side edge of the support rib being coupled to the groove's inner sidewall, and the other side edge of the support wall being coupled to the groove's outer sidewall. As depicted, the groove inner and outer sidewall locations at which the support rib attaches are at the same clock position centered on the wiper seal (the 12, 4, and 8 o'clock positions are shown), and the serpentine folds in the rib extend on both sides of this clock position.

Figure 3Q:
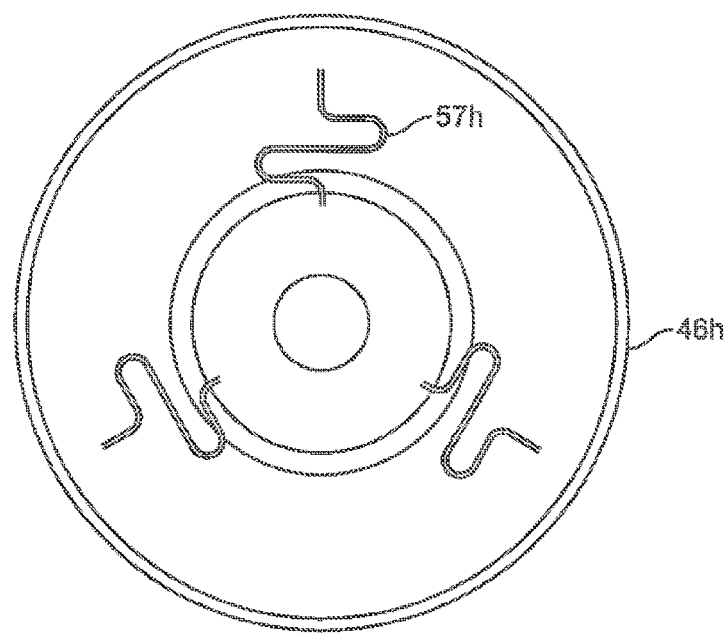
Figure 3R:
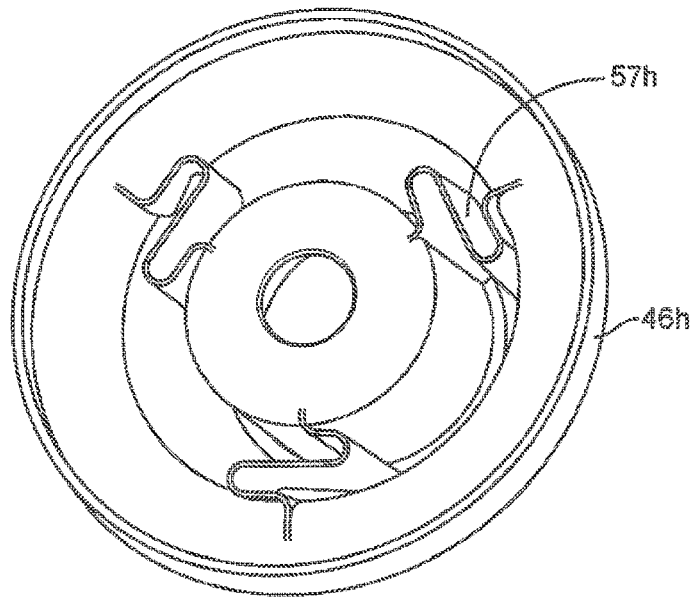

FIG. 3Q and FIG. 3R are top and perspective views of a wiper seal 46*h*, in which equally-spaced support ribs 57*h* are each positioned in a flex portion groove. The configuration of each support rib 57*h* is a serpentine S-curve similar to support ribs 56*g* (FIGS. 3O and 3P), except that the serpentine folds in support ribs 57*h* extend farther along the clock face (i.e., have a larger magnitude) than the serpentine folds in support ribs 57*g*.

Figure 3S:
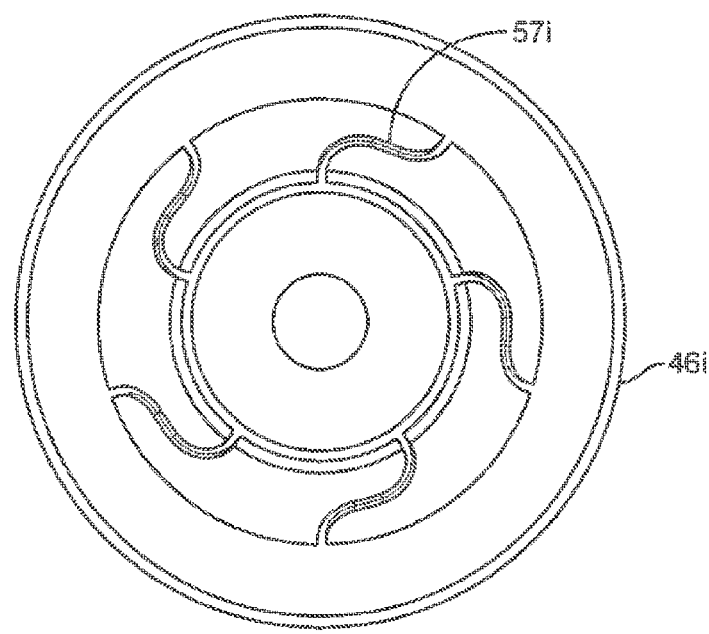
Figure 3T:
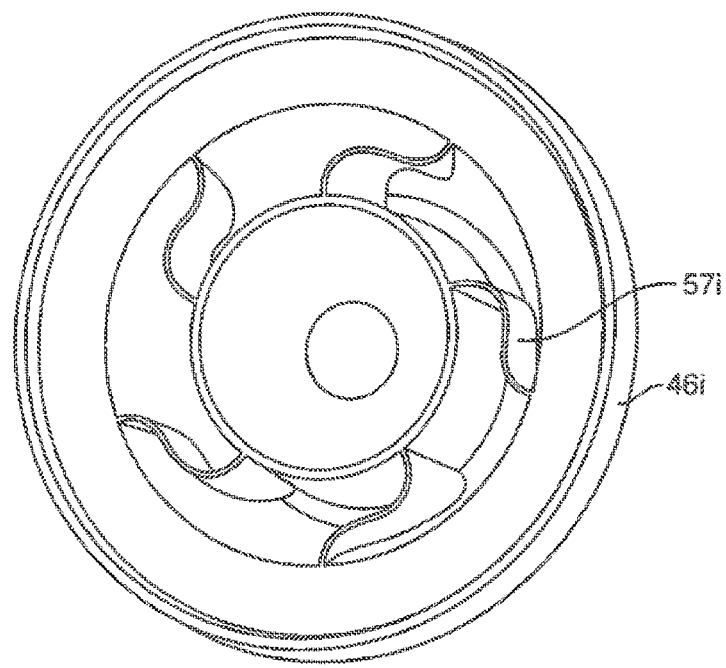

FIG. 3S and FIG. 3T are top and perspective views of a wiper seal 46*i*, in which equally-spaced support ribs 57*i* are each positioned in a flex portion groove. The configuration of each support rib 57*i* is a serpentine S-curve, with one side edge of the support rib being coupled to the groove's inner sidewall at one clock position centered on the wiper seal, and the other side edge of the support rib being coupled to the groove's outer sidewall an another clock position (e.g., displaced clockwise, as shown). As shown in FIGS. 3S and 3T, the serpentine folds do not extend beyond the clock positions at which the support rib attaches to the sidewalls. And the clock positions at which each support rib attaches to the groove's inner side wall is different from the clock position at each support rib attaches to the groove's outer side wall. As shown, for example, one rib is attached to the inner side wall at the 12 o'clock position and to the outer side wall at the 1 o'clock position.

Figure 3U:
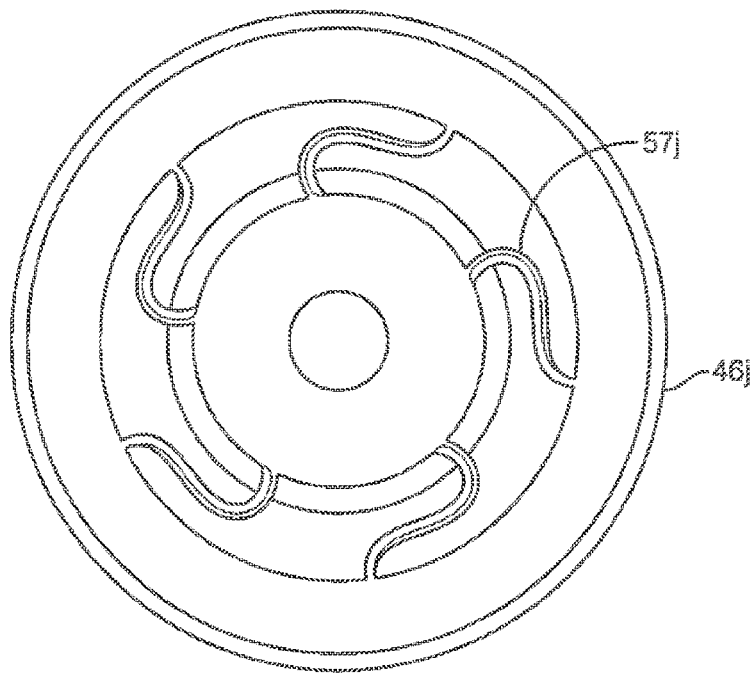
Figure 3V:
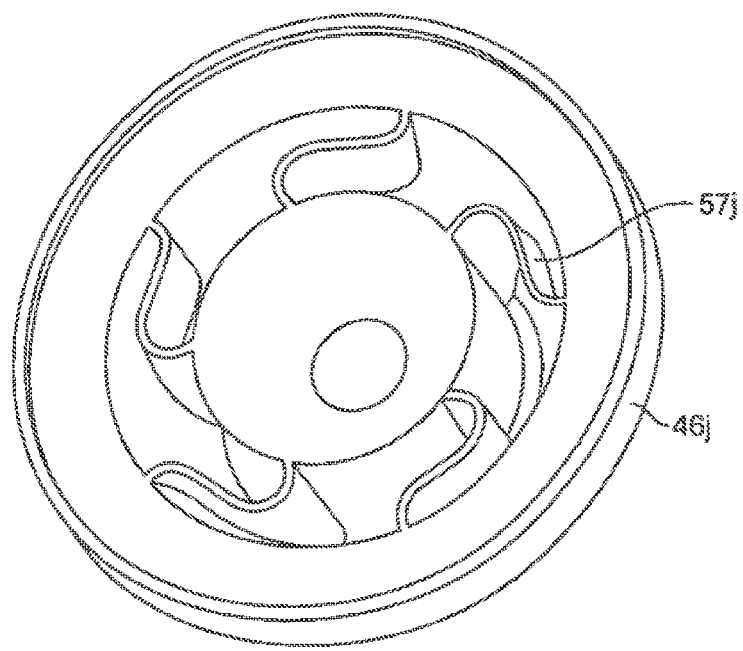

FIG. 3U and FIG. 3V are top and perspective views of a wiper seal 46*j*, in which equally-spaced support ribs 57*j* are each positioned in a flex portion groove. The configurations of each support rib 57*j* is similar to the configuration of support ribs 57*i* (FIGS. 3S and 3T), except that one of the serpentine folds of the support rib (e.g., the fold closer to the sealing portion, as shown), extends beyond the clock position at which the support rib attaches to the sidewalls.

Figure 3W:
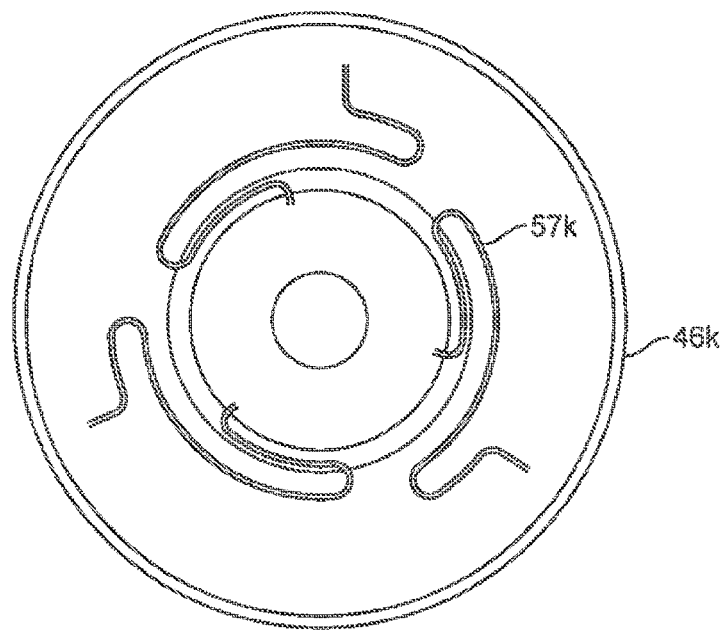
Figure 3X:
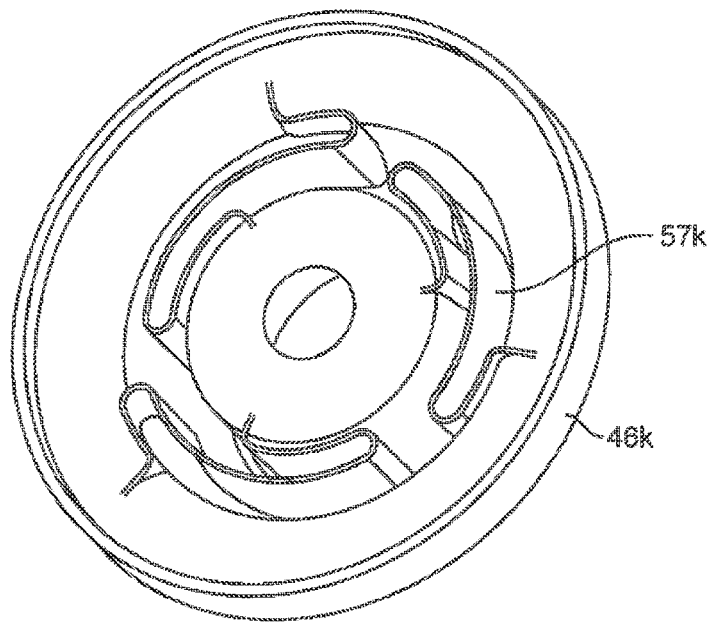

FIG. 3W and FIG. 3X are top and perspective views of a wiper seal 46*k*, in which equally-spaced support ribs 57*k* are each positioned in a flex portion groove. The configurations of each support rib 57*k* is similar to the configuration of support ribs 57*i* (FIGS. 3S and 3T), except that both of the serpentine folds of the support rib extend beyond the clock positions at which the support rib attaches to the sidewalls. This implementation, along with the implementation shown in FIGS. 3U and 3V, illustrate that the serpentine folds in the support rib are not necessarily symmetrical.

Figure 3Y:
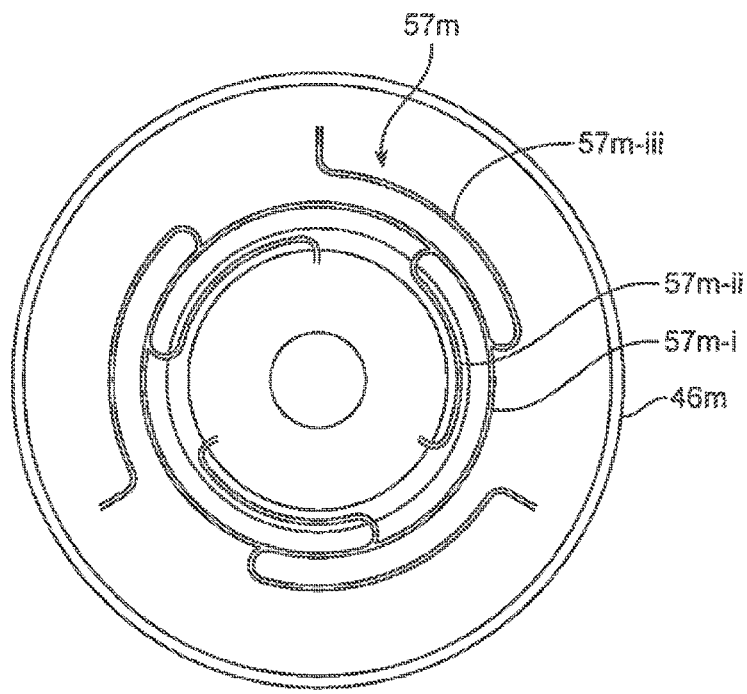
Figure 3Z:
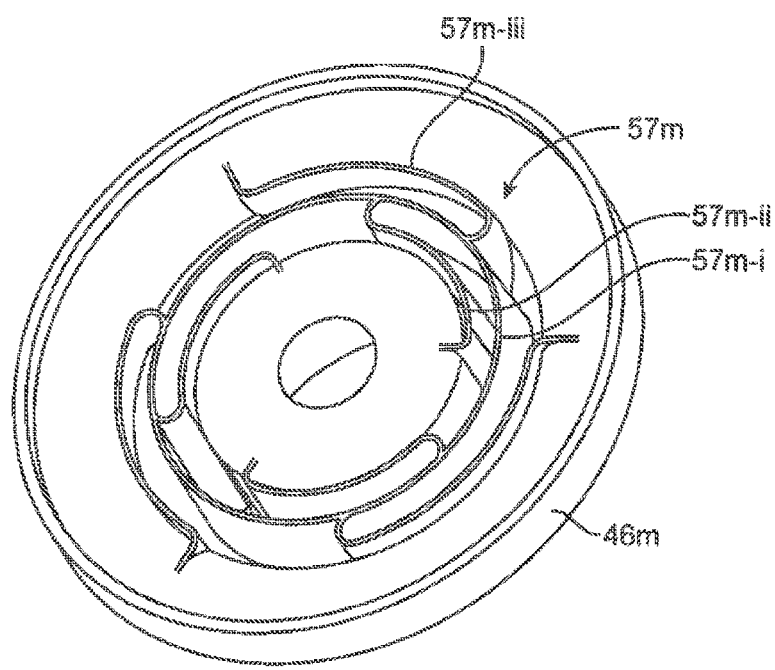
Figure 3A:
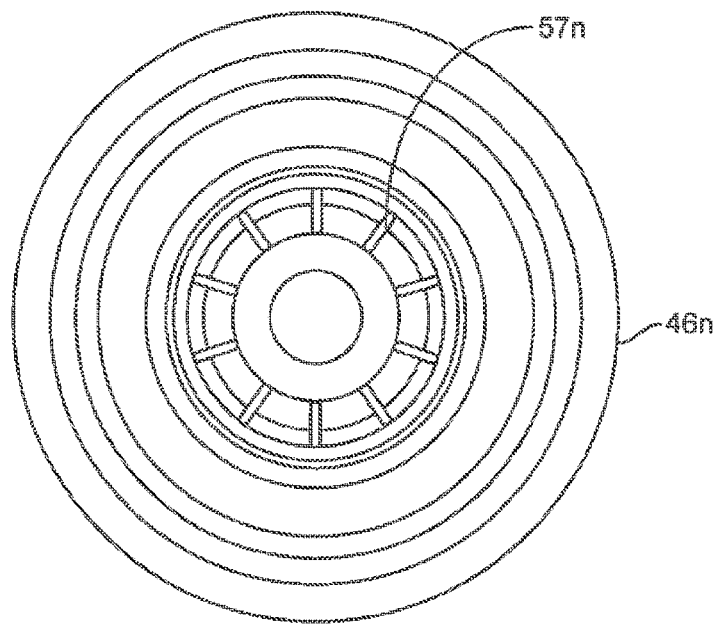
Figure 3A:
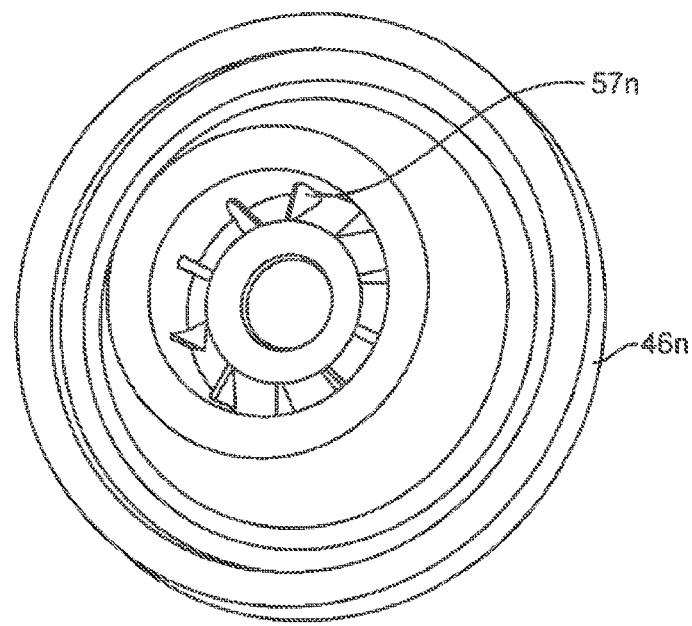

FIG. 3Y and FIG. 3Z are top and perspective views of a wiper seal 46*m*, in which equally-spaced support ribs 57*m* are each positioned in a flex portion groove. Support ribs 57*m* are a compound variation of support ribs generally described in FIGS. 3S to 3X. As shown, a longitudinally-oriented annular wall (i.e., a cylinder) 57*m-i* is positioned between the groove's sidewalls, and then serpentine support ribs are coupled between the groove's inner sidewall and the annular wall, and between the annular wall and the groove's outer sidewall. As shown, for example, support rib portion 57*m-ii* is coupled between the groove's inner sidewall and annular wall 57*m-i*, and support rib portion 57*m-iii* is coupled between annular wall 57*m-i* and the groove's outer sidewall. Each support rib portion 57*m-ii* and 57*m-iii* is configured similarly to support ribs 57*i* (FIGS. 3S and 3T), although other configurations may be used. The support rib configurations shown in FIGS. 3Y and 3Z illustrate that a web of interconnected support ribs can be positioned in one or more of the grooves in the wiper seal's flex portion. Implementations include any support rib configuration.

FIG. 3AA and FIG. 3AB are top and perspective views of a wiper seal 46*n*, in which equally-spaced support ribs 57*n* are each positioned in such a groove. As shown, support ribs 57*n* are each straight, radial ribs between the groove's inner and outer sidewalls. Ribs 57*n* provide strong resistance to stretching, and so provide a good seal anti-inversion feature if, for example, positioned in the wiper seal flex portion's innermost lower groove, as shown. For relatively small radial motions of the wiper seal's sealing portion (e.g., from small increases in instrument shaft diameter or small lateral motions), ribs 57*n* rely on their material's resilient compressibility. And for relatively larger radial motions of the wiper seal's sealing portion, ribs 57 rely on their material resiliently buckling.

Referring to FIG. 2, it can be seen that wiper seal 44 is optionally sized so that upper annular fold 51 is generally below (distal of) the annular distal end of instrument insertion guide 37. This configuration also helps to prevent wiper seal 44 from inverting when an instrument is withdrawn, because instrument insertion guide 37 helps prevent the relatively thick and less flexible sealing portion 46 from moving proximally as the instrument is withdrawn. Further, instrument insertion hole 38's diameter is sized to inwardly overhang sealing portion 46's outer perimeter so that the tip of an instrument being inserted will tend to contact sealing portion 46's angled upper face 48, and so be urged to pass through and not puncture or tear wiper seal 44. As shown, for example, instrument insertion hole 38's diameter is less than the outer perimeter diameter of upper face 48, so that an inserted instrument tip will first contact upper face 48 of the thick sealing portion 46. In this configuration, the instrument tip is guided away from contacting, and potentially damaging, the relatively thin flex portion 47.

It can also be seen in FIG. 2 that there is sufficient space between lower annular fold 53 and backflow prevention seal 42's inner folded sidewall, which allows sealing portion 46 to move distally and laterally without contacting the backflow prevention seal. In some implementations, such as those in which spacer 43 is made relatively thinner or is omitted, flex portion 47 may contact backflow prevention seal 42's inner sidewall, and the angle of the flex portion 47 outer sidewall at or near the contact location still allows sealing portion 46 to move distally and laterally.

In an example embodiment, wiper seal 44 is made of a medical grade elastomeric material, such as chlorinated polyisoprene or other rubber material, such as silicone, urethane, etc. Other suitable materials may be used.

Second Example

Figure 5:
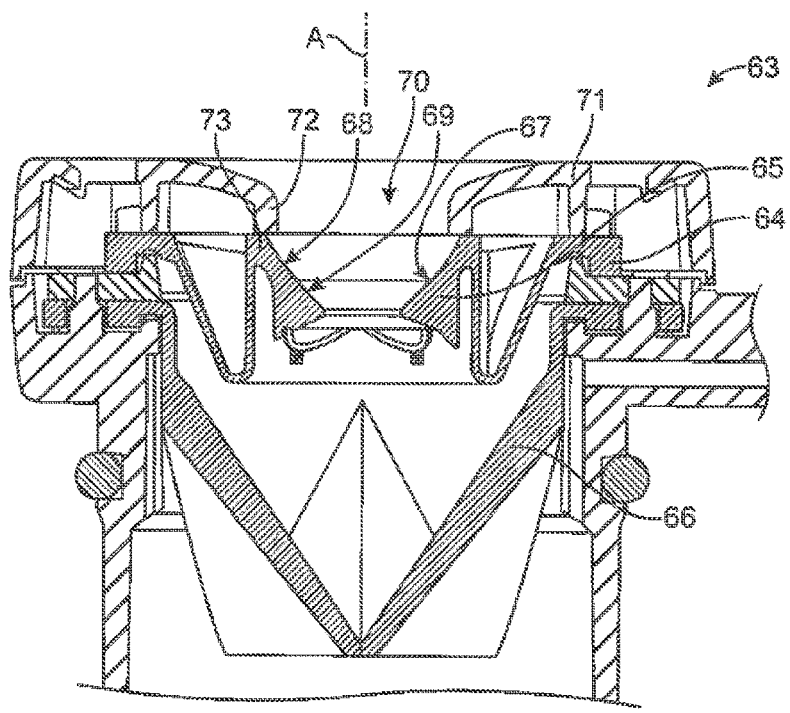
FIG. 5 is a cross-sectional elevation view of a portion of another example seal assembly embodiment.

FIG. 5 is a cross-sectional elevation view of a portion of another seal assembly embodiment 63, whose configuration, components, features, and variations are generally similar to the other example seal assembly embodiments in this description. As shown in FIG. 5, seal assembly 63 includes wiper seal 64 (which includes sealing portion 65) and backflow prevention seal 66. The optional spacer (e.g., FIG. 2, element 45) between the wiper seal and the upper housing is omitted from the depicted embodiment so that the top surfaces of wiper seal 64 are coplanar for molding.

As shown, sealing portion 65 includes an annular upper face 67, which includes an upper (proximal) concave face portion 68 that smoothly transitions to a lower (distal) straight face portion 69. Upper annular face 67 is made similar to upper annular face 48 (FIG. 2). Instrument insertion hole 70 in housing 71 is sized so that instrument insertion guide 72 slightly inwardly overhangs upper concave face portion 68, as described above. In addition, the upper annular fold 73 of wiper seal 64's flex portion is in contact or near contact with instrument insertion guide 72's distal end. Annular fold 73's top surface is shown as optionally flat, and other top surface shapes may optionally be used to allow sealing portion 65 to smoothly move laterally underneath insertion guide 72's distal end.

Referring to FIG. 2, despite the advantages of the relation between insertion guide 37's distal end and sealing portion 46, if an instrument is initially inserted at an extreme off-longitudinal-axis orientation (e.g., an operating room person may rest the tip in the instrument insertion hole and then tilt the instrument up to align it for insertion; see e.g. FIG. 7), the tip may enter the small gap between the top of upper annular fold 51 and the bottom of instrument guide 37. It can be seen that in contrast to FIG. 2's wiper seal 44 and its sealing portion 46, in FIG. 5's wiper seal 64 the upper concave face portion 68 (and upper annular fold 73) is extended proximally to be close to or in contact with the upper housing 71 and its insertion guide 72. This contact or near contact helps prevent an off-axis-inserted instrument tip from contacting the flex portion outside of sealing portion 65, and it helps urge the off-axis-inserted instrument's tip through the wiper seal. Concave face portion 68's relatively more acute angle with reference to the seal assembly's longitudinal axis also helps prevent the instrument tip from catching on the sealing portion, and so urges the tip through the wiper seal without damaging the seal.

Third Example

Figure 6:
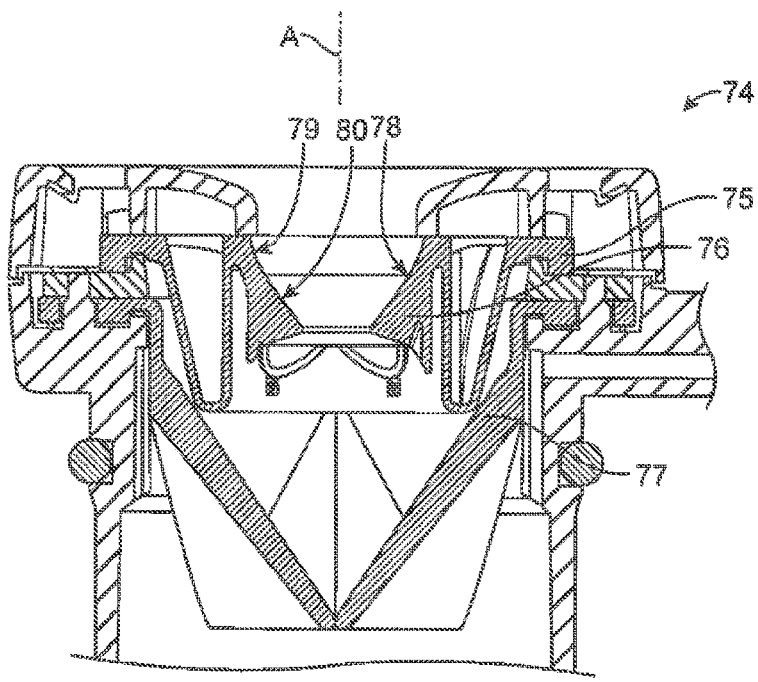
FIG. 6 is a cross-sectional elevation view of a portion of another example seal assembly embodiment.

FIG. 6 is a cross-sectional elevation view of a portion of another seal assembly embodiment 74, whose configuration, components, features, and variations are generally similar to the other example seal assembly embodiments in this description. As shown in FIG. 6, seal assembly 74 includes wiper seal 75 (which includes sealing portion 76) and backflow prevention seal 77. It can be seen that in contrast to wiper seal 64 (sec FIG. 5) and its sealing portion 65, wiper seal 75 and its sealing portion 76 are relatively deeper (i.e., longitudinally extended). Backflow prevention seal 77 is the same depth as backflow prevention seal 40 (FIG. 2), and in some embodiments it may optionally be made deeper to accommodate wiper seal 75 and its longitudinal movement. The optional spacer (e.g., FIG. 2, element 45) between the wiper seal and the upper housing is omitted from the depicted embodiment.

Similar to sealing portion 65 (FIG. 5), sealing portion 76 includes an annular upper face 78, which includes an upper concave face portion 79 that smoothly transitions to an annular lower straight face portion 80. Lower straight face portion 80 is formed to have a steeper angle than—and so has a radial width (surface area) larger than-straight face portion 69 (FIG. 5) with reference to an inserted surgical instrument (i.e., the face angle is more acute with reference to the seal assembly's longitudinal axis). Therefore, upper annular face 78 is relatively radially wider than upper annular face 67 (FIG. 5). Annular lower straight face portion 80's steep angle further helps urge an instrument tip through wiper seal without puncturing or tearing the relatively soft material used to form the wiper seal. As shown in FIG. 6, the mutually relative configurations of the instrument insertion guide and wiper seal are similar to the embodiment shown in and described with reference to FIG. 5.

Referring to FIGS. 2, 5, and 6, it can be seen that at the center of the wiper seal, the thick sealing portion's upper face can have many surface variations, which include flat, concave, and possibly convex annular surfaces, along with various combinations of such surfaces that blend into one another. Although not shown, it is envisioned that the sealing portion's lower face may have similar variations.

Fourth Example

FIG. 7 is a cross sectional elevation view of a portion of another seal assembly embodiment 81, whose configuration, components, features, and variations are generally similar to the other example seal assembly embodiments in this description. Seal assembly 81 includes a seal assembly housing 82, a backflow prevention seal 83, a wiper seal 84 proximal of backflow prevention seal 83, and an instrument insertion guide 85 positioned over (proximal of) wiper seal 84. Instrument insertion guide 85 is fixed to the seal assembly housing and defines an instrument insertion hole 86 in housing 82. Insertion guide may be formed as an integral piece of the seal assembly housing's upper portion, as shown, or it could optionally be formed as a separate that is then mechanically or adhesively joined to the upper housing.

As shown in FIG. 7, instrument insertion guide 85 extends distally into seal assembly housing 82 much farther (more distal) than, for example, instrument insertion guide 37 extends into seal assembly housing 21 (FIG. 2). A distal end of the instrument insertion guide extends to a depth distal of the location at which the wiper seal is coupled to the seal assembly housing. As depicted, instrument insertion guide 85 extends to a depth that is about 4/10ths of the distance (it could be more or less, such as 3/100ths or 5/10ths) between seal assembly housing 82's proximal end 87 and distal end 88. Stated another way, the instrument insertion guide 85 extends distally past the plane of the wiper seal's most proximal portion. Stated yet another way, in the wiper seal's flex portion upper groove, the groove's outer sidewall is longer than its inner sidewall (e.g., about two times longer or more) so that the wiper seal's sealing portion is to be near a longitudinal center of the sealing assembly. Instrument insertion guide 85's extended length further ensures that the distal tip of an instrument inserted into seal assembly 81 will contact the upper annular face 88 of wiper seal 84's sealing portion 89 at an angle relatively more acute than an angle the tip would contact the upper annular face if the instrument insertion guide had a shorter length, such as is illustrated in FIGS. 5 and 6. This enhanced instrument guide feature is illustrated by considering the insertion orientation of one surgical instrument 90, as shown in FIG. 7. The surgical instrument at insertion orientation 90a is about what it would be if the length of the instrument insertion guide was as shown in, for example, FIG. 2. Thus surgical instrument 90s's distal tip 91 at orientation 90a could contact the wiper seal's upper annular face at a steep angle, which increases the risk that tip 91 will puncture or tear the wiper seal, and which in some instances may even urge tip 91 away from passing through the wiper seal due to tip 91's contact angle with the annular face. In contrast, surgical instrument orientation 90b is limited by instrument insertion guide 85's length, so that surgical instrument 90's distal tip 91 will contact the wiper seal's upper annular face at a relatively more acute angle, thus reducing the risk that tip 91 will puncture or tear the wiper seal, and which ensures that the annular face will even more effectively urge tip 91 towards passing through the wiper seal. As shown, sealing portion 89 has a configuration similar to sealing portion 65 (FIG. 5), and it should be understood that various sealing portion configurations may be used.

As shown in FIG. 7, the lengths of backflow prevention seal 83 and wiper seal 84 are extended to accommodate instrument insertion guide 85's increased length. Seal assembly housing 81's overall length is generally limited by the depth of the cannula bowl (not shown; see FIG. 2) in which it is inserted. To prevent damage to backflow prevention seal 83 during normal handling, and to prevent the cannula bowl inner surface from interfering with backflow prevention seal 83's function when an instrument is inserted, backflow prevention seal 83's length is configured so that its distal end 92 does not extend past seal assembly 81's distal end 88 when backflow prevention seal 83 is in the closed (sealed) position. Wiper seal 84's sealing portion 89 may optionally be extended as far as possible into backflow prevention seal 83, so that backflow prevention seal 83 does not interfere with the proximal-distal and lateral movement of sealing portion 89 and its adjacent flex portion. As shown in FIGS. 7 and 3B, the outer surface of the flex portion's upper annular groove 93 may optionally be configured with thick, longitudinal stiffening ribs 94 to provide additional support for wiper seal 84's flex portion and to keep the wiper seal from inverting proximally at these outer walls. In one illustrative embodiment, each stiffening rib 94 is positioned between adjacent upper support ribs 95 with a width that is approximately one-half the distance between the support ribs. More or fewer stiffening ribs 94 may be used at various positions.

In addition, optional support ribs 96 may be placed around instrument insertion guide 85's outer surface, extending radially outward, to provide increased support for instrument insertion guide 85. The distal ends 97 of the radial support ribs 96 are optionally configured to have the same length as instrument insertion guide 85, so that the inner annular fold of the flex portion contacts both instrument guide 85's distal end 98 and the support ribs 96's distal ends 97 when an instrument is withdrawn through wiper seal 84. The distal ends 97 act as both a proximal longitudinal motion limit stop and a lateral motion guide surface. Thus sealing portion 89's proximal range of motion is limited regardless of its lateral position within the seal assembly housing. This proximal motion limit keeps the wiper seal from temporarily or permanently catching on the insertion guide when an instrument is removed, especially if the instrument is removed in a direction off the longitudinal axis.

Optional radial support ribs 99 may be placed under seal assembly 81's proximal end 87 to provide additional structural support. Support ribs 96 and 99 may optionally be blended together to form an approximately L-shaped support brackets that extend under the upper housing's top surface and then distally along the outside of instrument guide 85.

Fifth Example

Figure 8:
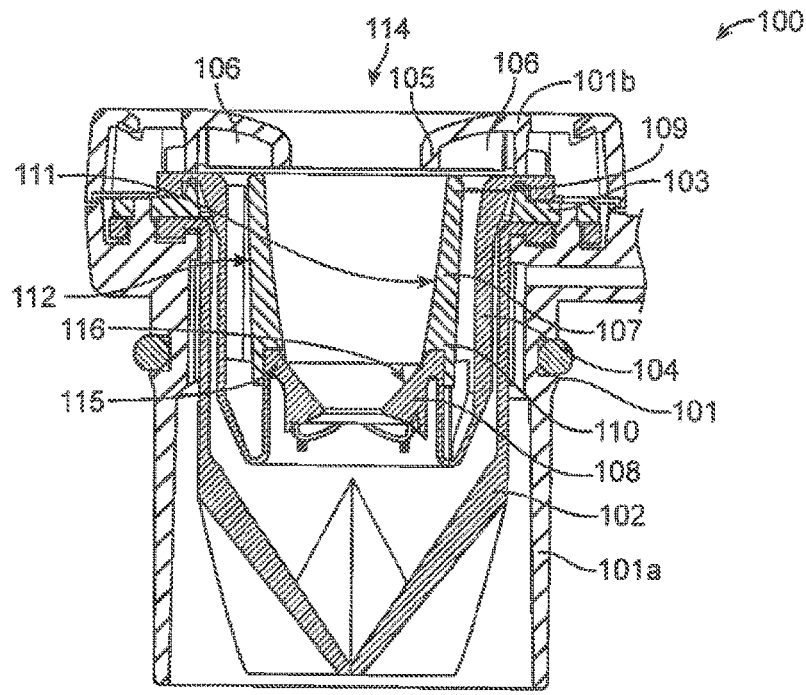
FIG. 8 is a cross-sectional elevation view of a portion of another example seal assembly embodiment.

FIG. 8 is a cross-sectional elevation view of a portion of another seal assembly embodiment 100, whose configuration, components, features, and variations are generally similar to the other example seal assembly embodiments in this description. FIG. 8 shows that seal assembly 100 includes seal assembly housing 101 (which includes lower housing 101a and upper housing 101b), backflow prevention seal 102 positioned distally within lower housing 101a, spacer (and optional latch mechanism) 103 positioned over (proximal of) backflow prevention seal 102, wiper seal 104 positioned over (proximal of) spacer 103, and upper housing 101b positioned over (proximal of) wiper seal 104. Upper housing 101b includes an integrally formed, short, fixed instrument insertion guide 105 and support ribs 106 extending radially outward from insertion guide 105 underneath the top of proximal housing 101b, similar to the seal assembly 20 configuration illustrated in FIG. 2.

Wiper seal 104 is configured generally similar to wiper seal 84's configuration, as illustrated in FIG. 7. In contrast to the seal assembly illustrated in FIG. 7, however, seal assembly 100 includes a second, floating instrument insertion guide 107 that is attached to wiper seal 104's sealing portion 108, so that instrument insertion guide 107 moves proximally-distally (longitudinally) and also laterally as sealing portion 108 moves.

As depicted in FIG. 8, floating instrument insertion guide 107 is generally cylindrically shaped, with a proximal end 109, a distal end 110, an inner side wall surface 111, and an outer sidewall surface 112. In one embodiment, instrument insertion guide 107's proximal end 109 optionally touches, or nearly touches, the bottoms of radial support ribs 106, which prevent instrument insertion guide 107's further proximal movement (and wiper seal 104 from inverting, as described above) and provide a lateral movement guide surface for insertion guide 107. Thus proximal end 109 may smoothly slide laterally while being kept at its proximal range-of-motion limit by the bottoms of radial support ribs 106. The distal end of fixed instrument insertion guide 105 may optionally be made flush with the bottoms of support ribs 106, or it may extend beyond the bottoms of support ribs 106. Alternatively, an optional spacer may be positioned between upper housing 101b and distal end 109, so that the spacer limits floating instrument insertion guide 107's proximal travel. (See e.g., FIG. 13A, anti-inversion piece 152, or a similar ring without flexible fingers 154, is an illustrative spacer.) Instrument insertion guide 105 inwardly overhangs floating instrument insertion guide 107 proximal end 109, so that the diameter of instrument insertion hole 114 in proximal housing 101a is less than the diameter defined by floating instrument insertion guide 107's inner sidewall surface 111 at proximal end 109. Thus floating instrument insertion guide 107 may move laterally to its extreme range of motion without distal end 109 being exposed through hole 114, so that no portion of the instrument being inserted will catch on a portion of distal end 109 during instrument insertion.

Floating instrument insertion guide 107's distal end 110 is in contact with the outer perimeter of wiper seal 104's sealing portion 108. As shown, distal end 110 is in contact at or near upper annular fold 115, where sealing portion 108 joins wiper seal 104's flex portion. FIG. 8 shows that floating instrument insertion guide 107's outer sidewall 112 may optionally extend below the top of annular fold 115 to provide increased support for the contact between wiper seal 104 and floating instrument insertion guide 107 (cutouts, or other distal end 110 configurations, to accommodate support ribs in the flex portion may be included, depending on the support rib configuration). Likewise, FIG. 8 shows that floating instrument insertion guide 107's inner sidewall 111 may optionally extend below the top of annular fold 115 to provide a smooth transition between sidewall 111 and sealing portion 108's upper face 116. As depicted, an outer portion of sealing portion 108's upper face 116 is concave, as described above, to further provide a smooth surface transition between sidewall 111 and upper face 116. In some embodiments, floating instrument insertion guide 107 merely rests against wiper seal 104 and is held in place by the configuration of the assembly. In other embodiments, floating instrument insertion guide 107 may be secured to wiper seal 104 by, for example, an adhesive or a bonding process (e.g., using Loctite®, 4011™), or by mechanical attachment. In addition, skilled artisans will understand that the instrument insertion guide may be attached at various locations on the wiper seal that will allow the insertion guide to move laterally within the seal assembly housing.

As shown in FIG. 8, floating instrument insertion guide 107's inner sidewall 11 is optionally made slightly concave to help guide an instrument tip towards, and provide a smooth transition to, the upper surface of wiper seal 104's sealing portion 108. In other embodiments, however, other floating instrument insertion guide inner sidewall configurations (e.g., flat, convex, compound, etc.) may be used as illustrated below.

Sixth Example

Figure 9:
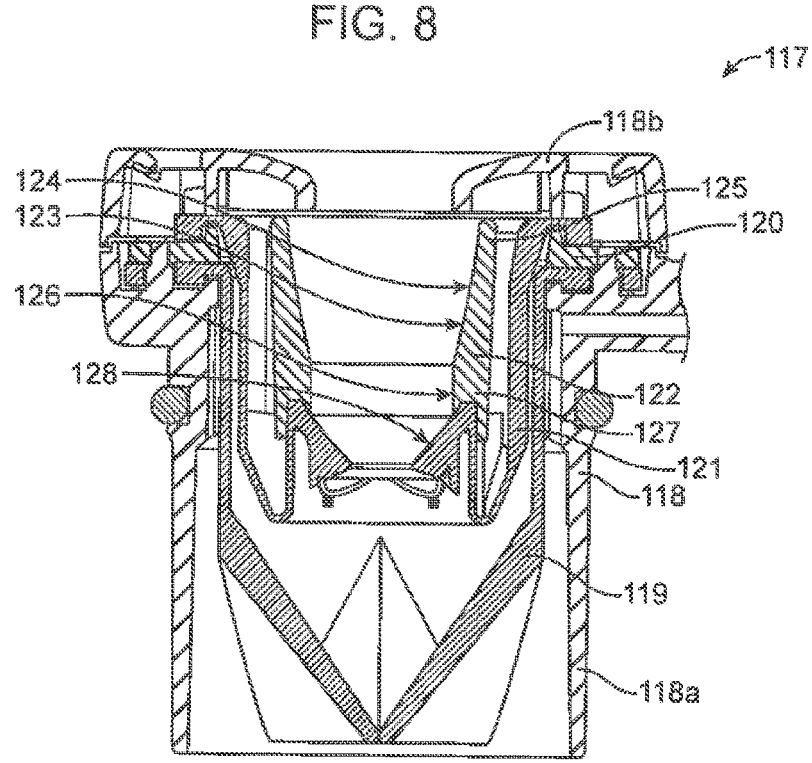
FIG. 9 is a cross-sectional elevation view of a portion of another example seal assembly embodiment.

FIG. 9 is a cross-sectional elevation view of a portion of another seal assembly embodiment 117, whose configuration, components, and variations are generally similar to the other example seal assembly embodiments in this description. FIG. 9 shows seal assembly 117 includes seal assembly housing 118 (which includes lower housing 118a and upper housing 118b), backflow prevention seal 119 positioned distally within distal housing 118a, spacer (and optional latch mechanism) 120 positioned over (proximal of) backflow prevention seal 119, wiper seal 121 positioned over (proximal of) spacer 120, and proximal housing 118b positioned over (proximal of) wiper seal 121. Seal assembly 117 also includes floating instrument insertion guide 122, which along with the various other associated seal assembly 117 components is generally configured as described with reference to seal assembly 100 (FIG. 8). FIG. 9 illustrates alternate configurations of the floating instrument insertion guide's interior sidewall.

As shown in FIG. 9, floating instrument insertion guide 122's inner sidewall 123 includes an upper portion 124 adjacent its proximal end 125, and upper portion 124 smoothly transitions to a lower portion 126 adjacent its distal end 127. Upper portion 124 is slightly concave (or optionally straight or convex), and lower portion 126 is flat (or optionally concave or convex). Lower portion 126's cylindrical, vertical side walls form a relatively less acute angle transition to wiper seal 121's sealing portion upper face 128 than, for example, the transition illustrated in FIG. 8. Nevertheless, it has been found that lower portion 126's vertical sidewalls limit the insertion orientation angle of the instrument itself, and the result is improved instrument tip insertion through wiper seal 121 with less tendency for the instrument tip to catch on upper face 128. Thus it can be seen that many floating instrument insertion guide inner sidewall configurations exist. In addition, it is possible to optionally similarly configure the inner sidewalls of fixed instrument insertion guides (see e.g., instrument insertion guide 85 in FIG. 7) in the seal assembly housing.

Seventh Example

Figure 10:
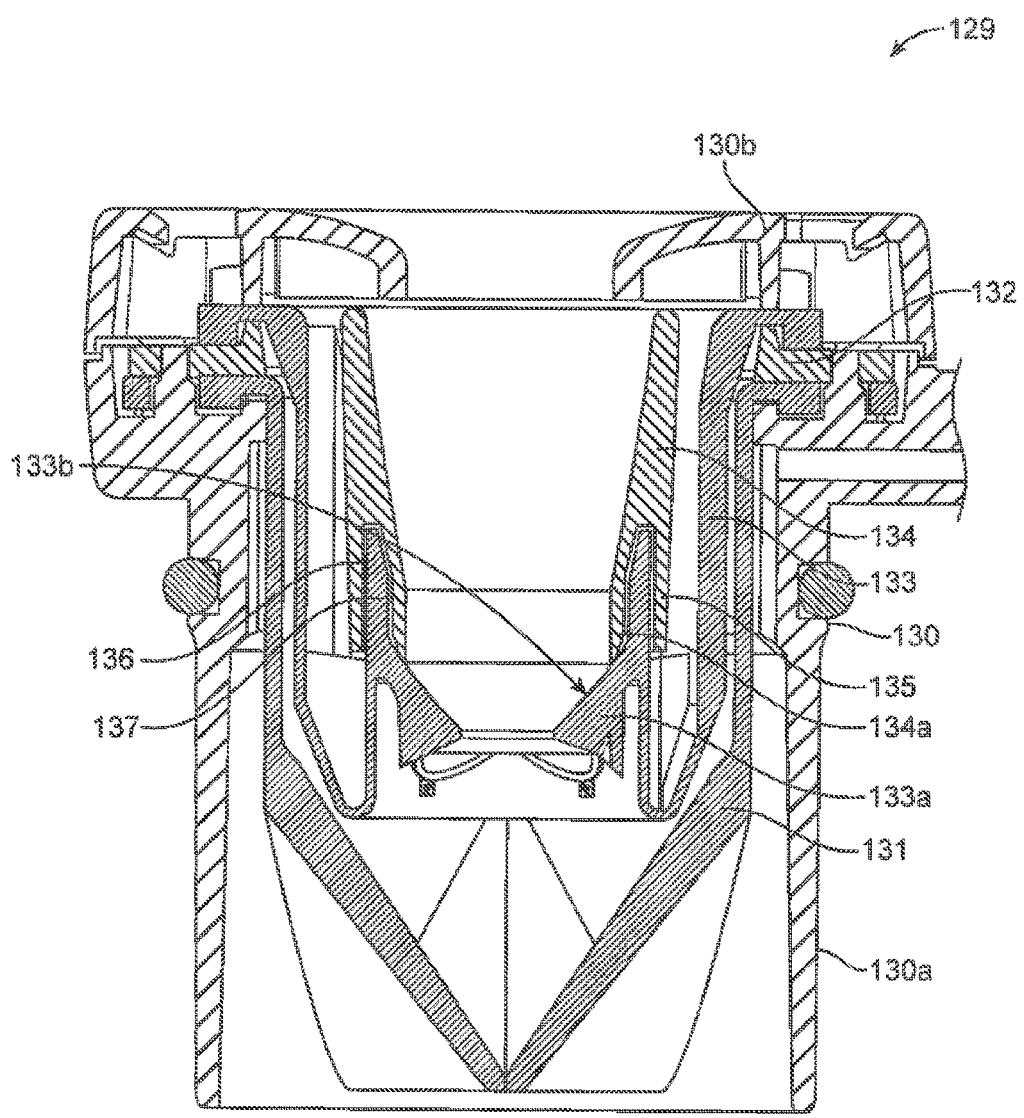
FIG. 10 is a cross-sectional elevation view of a portion of another example seal assembly embodiment.

FIG. 10 is a cross-sectional elevation view of a portion of another seal assembly embodiment 129, whose configuration, components, features, and variations are generally similar to the other example seal assembly embodiments in this description. FIG. 10 shows seal assembly 129 includes seal assembly housing 130 (which includes lower housing 130a and upper housing 130b), backflow prevention seal 131 positioned distally within lower housing 130a, spacer (and optional latch mechanism) 132 positioned over (proximal of) backflow prevention seal 131, wiper seal 133 positioned over (proximal of) spacer 132, and upper housing 130b positioned over proximal of) wiper seal 133. Seal assembly 129 also includes floating instrument insertion guide 134, which along with the various other associated seal assembly 129 components is generally configured as described with reference to seal assemblies 100 (FIG. 8) and 117 (FIG. 9). FIG. 10 illustrates alternate configurations of the floating instrument insertion guide's distal end 135 and corresponding wiper seal portion.

As shown in FIG. 10, floating instrument insertion guide 134's distal end 135 includes an annular groove 136 between the insertion guide's inner and outer sidewall surfaces. Wiper seal 133 includes an annular boss 137 that extends upward (proximally) from the location at which wiper seal 133's sealing portion joins to its flex portion. Annular boss 137 fits inside annular groove 136 to help secure floating instrument insertion guide 134 to wiper seal 133. In the depicted embodiment, the deepest (most proximally oriented when assembled) part of annular groove 136 is tapered so that sufficient material thickness exists between the groove sidewall and the insertion guide's inner sidewall, and the interior of the corresponding proximal portion of annular boss 137 is beveled to match the tapered shape. A small clearance exists between annular groove 136 and annular boss 137 to ensure that the distal end 134a of instrument guide 134 contacts the upper annular face 133b of wiper seal 133's sealing portion 133a to form a smooth surface transition between the two components. The clearance also ensures sufficient space for a bonding adhesive to be used to bond annular boss 137 and insertion guide 134. An optional mechanical attachment may be used. This mating configuration between wiper seal 133 and floating instrument insertion guide 134 helps resist lateral forces from an instrument tip that may separate wiper seal 133 and instrument insertion guide 134 as an instrument is inserted into and through seal assembly 129.

Seal Assembly Latch

Figure 11:
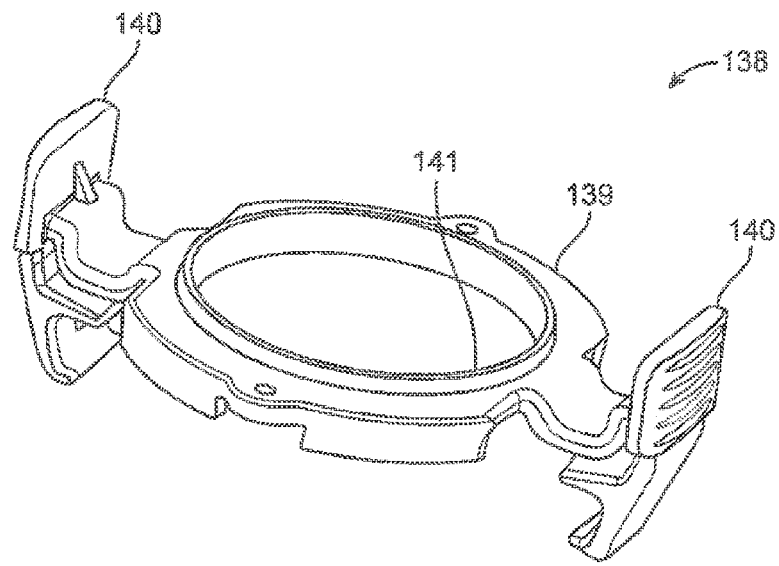
FIG. 11 is a perspective view of an example combination spacer and latch piece for a seal assembly.

FIG. 11 is an upper perspective view of a combination spacer and latch piece 138 for a seal assembly, which includes a ring-shaped spacer portion 139 and two latches 140 positioned opposite one another at the outer perimeter of spacer portion 139. At spacer portion 139's inner perimeter, a raised annular boss 141 extends proximally. As shown, spacer portion 139 and latches 140 are integrally formed as a single piece. In one example embodiment, the combination spacer and latch piece 138 is made of flexible polycarbonate, and other materials may be used if they offer suitable flexibility for the U-shaped flexures, described below. And, although two latches 140 are shown, other embodiments include a single latch and three or more latches. As discussed below, a single latch in accordance with the disclosed aspects will effectively latch the seal assembly to the cannula.

The spacer portion 139 functions as generally shown and described above (FIG. 2 no. 43; FIG. 8 no. 103; FIG. 9 no. 120; FIG. 10 no. 132). When spacer and latch piece 138 is assembled into a seal assembly, annular boss 141 is aligned between portions of the upper and lower seal assembly housings, so that the wiper seal's perimeter portion is sandwiched and compressed between the upper housing piece and the annular spacer portion 139, and the backflow prevention seal's perimeter portion is sandwiched and compressed between the lower housing piece and the annular spacer portion 139. The slight compression forms a gas-tight seal. Annular boss 141 may optionally be positioned at or near spacer portion 139's outer perimeter, or between its inner and outer perimeters. In some implementations, the annular boss may extend distally. Two or more annular bosses may be used in various combinations.

Figure 12:
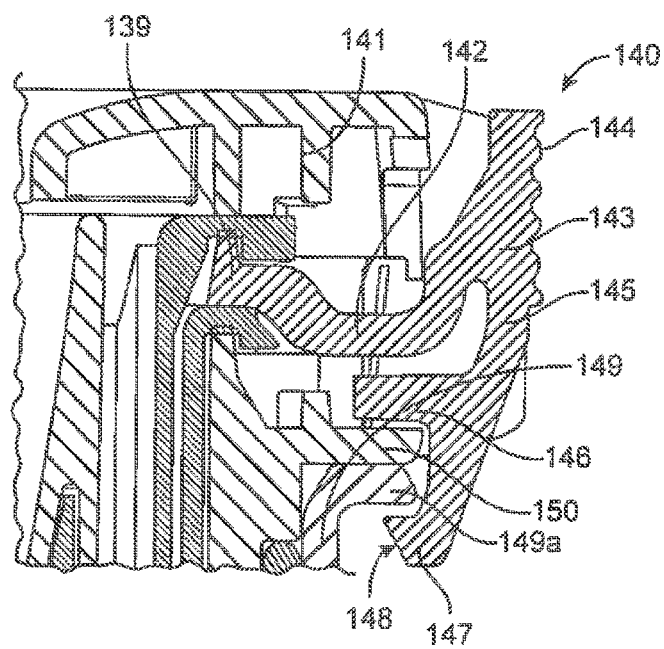
FIG. 12 is a cross-sectional view of an example latch portion of the spacer and latch piece shown in FIG. 11, with an example coupling of a seal assembly to a cannula.

FIG. 12 is a cross-sectional view of a latch portion 140 of spacer and latch piece 138 within a seal assembly coupled to a cannula. Latch portion 140 includes a U-shaped resilient flexure 142 that joins to spacer portion 139 at one end. At the other end, flexure 142 joins to a middle area of latch piece 143. Above (proximal of) the middle area at which flexure 142 joins latch piece 143 is a finger tab 144 patterned to assist grip (e.g., grip by a surgical-glove-covered digit). Below (distal of) the middle area is a latch tab 145 that includes a finger 146 that extends laterally inward towards spacer portion 139, and below finger 146 is a catch 147 oriented inward toward spacer portion 139. Catch 147 optionally includes an inward-oriented distal beveled lead-in surface 148 to help catch 147 flex radially outward and then latch to the cannula as the seal assembly is pressed into the cannula bowl.

In use, latch piece 143 pivots around a fulcrum defined by flexure 142, so that as finger tab 144 moves radially inward, latch tab 145 moves radially outward. When the seal assembly is inserted into a cannula bowl at the proximal end of a cannula, lead-in surface 148 contacts cannula bowl flange 149a, which causes latch tab 145 to move outward. Once catch 147 is distal of cannula bowl flange 149a, flexure 142 returns latch tab 145 to its original position, and so positions catch 147 under cannula bowl flange 149a, thus removably latching the seal assembly to the cannula 149. Latch portion 140 is sufficiently resilient to latch the cannula bowl without squeezing the finger tabs 144 when the seal assembly is pressed into the cannula bowl, and it is sufficiently stiff to prevent the seal assembly from disengaging from the cannula bowl until the finger tabs 144 are squeezed.

As shown in FIG. 12, when the seal assembly is latched to a cannula bowl, cannula bowl flange 149a and seal assembly housing relief surface (shoulder) 150 are positioned between catch 147 and finger 146's bottom (distal) surface. As a result, if an attempt to remove the seal assembly from the cannula bowl is made, catch 147 contacts the bottom of cannula flange 149a, and the top (proximal) surface of seal assembly housing relief surface (shoulder) 150 contacts the bottom surface of finger 146, which keeps the seal assembly from being removed from the cannula bowl. An advantage of this latch configuration is that the retention force is kept between catch 147 and finger 146 without being transferred to flexure 142. And in addition, latch tab 145's design allows the seal assembly to rotate around the longitudinal axis without limit inside the cannula bowl, as described in more detail below. Further, if only one of the two latch portions is engaged with the cannula flange, then a proximal pulling force on the seal assembly will tend to rotate the seal assembly around the engaged latch portion, then the bottom of the seal assembly housing (see e.g., FIG. 2, no. 22) will contact an inner sidewall of the cannula bowl, and the seal assembly is prevented from being removed from the cannula. Thus both latch portions 140 must be released by squeezing finger tabs 144 to remove the seal assembly from the cannula. Inadvertent latch release may be further prevented by positioning physical guards near the finger tabs 144, as described below (see e.g., FIG. 13B, elements 157).

Anti-Inversion Piece

Figure 13A:
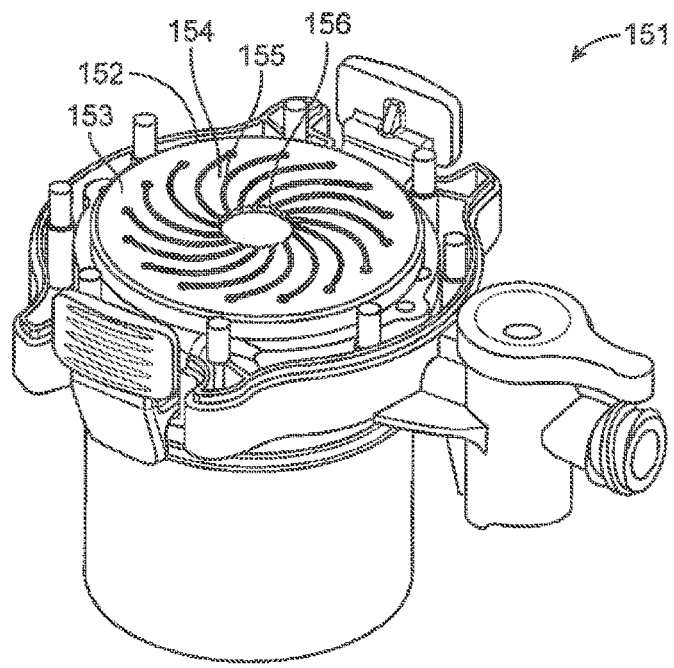
FIG. 13A is a top perspective view of an example seal assembly with a top portion of its housing removed to show an example embodiment of an optional seal anti-inversion piece.
Figure 13B:
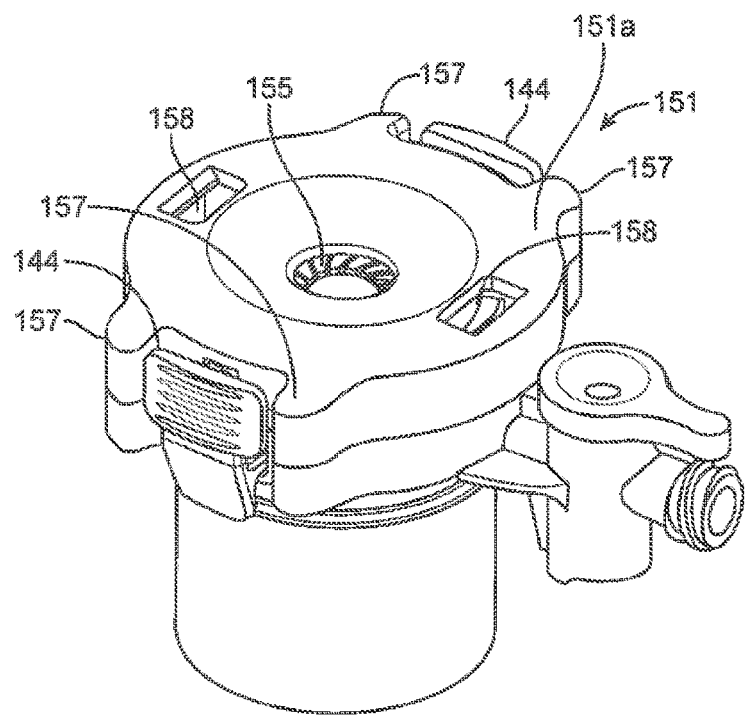
FIG. 13B is a top perspective view of the seal assembly with the top portion of its housing in place.

FIG. 13A is a top perspective view of an example seal assembly 151 with a top portion of its housing removed to show an example embodiment of an optional seal anti-inversion piece 152 positioned over (proximal of) the wiper seal, and FIG. 13B is a top perspective view of seal assembly 151 with the top portion of its housing in place. As shown in FIGS. 13A and 13B, anti-inversion piece 152's outer perimeter area 153 functions as a spacer between a top perimeter surface of the wiper seal and a bottom surface of the top portion of the seal assembly housing (see e.g., FIG. 2, spacer 45). Anti-inversion piece 152 includes several (16 are shown) anti-inversion fingers 154 that extend from outer perimeter area 153 radially inward, and the tips 155 of fingers 154 define a center hole 156, through which a surgical instrument is inserted. Hole 156's diameter may optionally be larger than, equal to, or less than the smallest diameter surgical instrument shaft that seal assembly 151 is designed to accommodate. As depicted, fingers 154 are optionally formed in a spiral pattern, and other patterns (e.g., extending straight inward, extending inward at an angle, etc.) may be used. In a more general sense, therefore, the fingers may optionally be configured in two ways-one type in which the tips of the fingers are radially aligned with the finger hinge points near the outer perimeter, and another type in which the tips of the fingers are radially offset (clockwise or counter-clockwise) from the finger hinge points near the outer perimeter.

Anti-inversion piece 152 is flat and is made of a stiff but resilient material, so that if the fingers 154 are flexed downward (distally) when an instrument is inserted, anti-inversion piece 152 returns to its flat configuration when the instrument is withdrawn. Unlike straight, radial fingers, the spiral pattern fingers can move radially outward and overlap to avoid being caught in a portion of an instrument being withdrawn. Other finger patterns, including straight, radial fingers, may be used, as described below.

As shown in FIG. 13B, the upper portion of the seal assembly housing extends radially inward part-way over the fingers, so that only the tips 155 are visible through the instrument insertion hole in the top of the seal assembly housing. In operation, the fingers 154 are sufficiently long to easily flex downward when a surgical instrument is inserted in the seal assembly. When the instrument is withdrawn, the fingers prevent the underlying wiper seal from inverting through the instrument insertion hole at the top of the seal assembly housing. By allowing the tips 155 to extend slightly into a longitudinal cylinder defined by the housing's instrument insertion hole, if one or more tips 155 catch on a part of the instrument (e.g., a wrist assembly or surgical end effector), then the tip(s) may flex slightly upward (proximally) through the hole to allow the instrument to be withdrawn. The upper housing's inner perimeter that defines the hole acts as a fulcrum for the tips 155 when the instrument flexes the tips upwards. The tips 155 are optionally rounded and/or lubricated to reduce friction between the tips and the surgical instrument shaft during normal use. In one embodiment, the anti-inversion piece 152 is made of high-density polyethylene with two percent siloxane (i.e., HDPE with infused silicon for lubricity). Other flexible, durable plastics may be used.

Figure 13C:
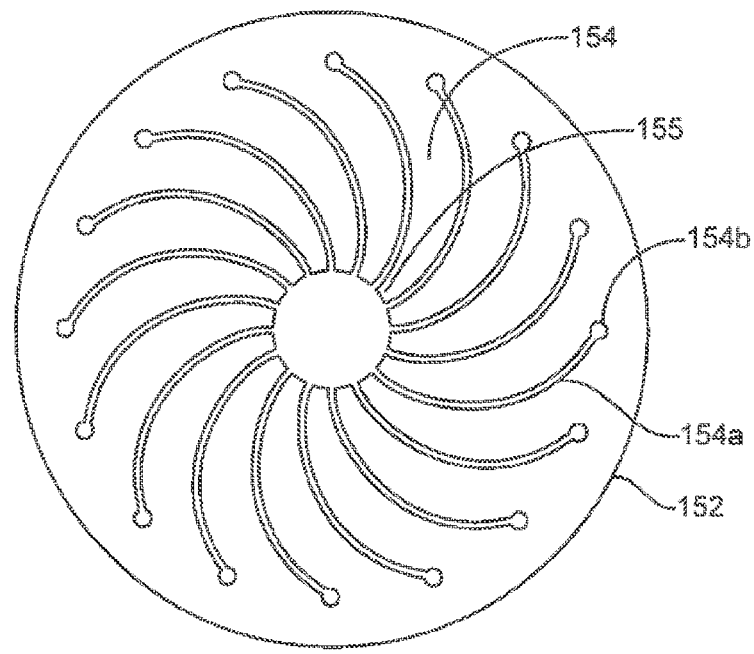
FIGS. 13C-13I are plan views of various anti-inversion piece configurations.

FIG. 13C is a plan view of anti-inversion piece 152. As shown, 16 equal-length spiral-pattern fingers 154 are defined by 16 corresponding spiral-pattern cuts 154a. A crack-stop hole 154b is defined at the outward radial end of each cut 154a to help prevent material failure as the fingers flex distally and are displaced radially outward. Such crack-stop holes may optionally be used on all anti-inversion piece embodiments. As shown, the tips 155 of each of the fingers 154 are generally squared off, and they may optionally be rounded to help prevent catching in surgical instrument components and reduce friction against the instrument shaft.

Figure 13D:
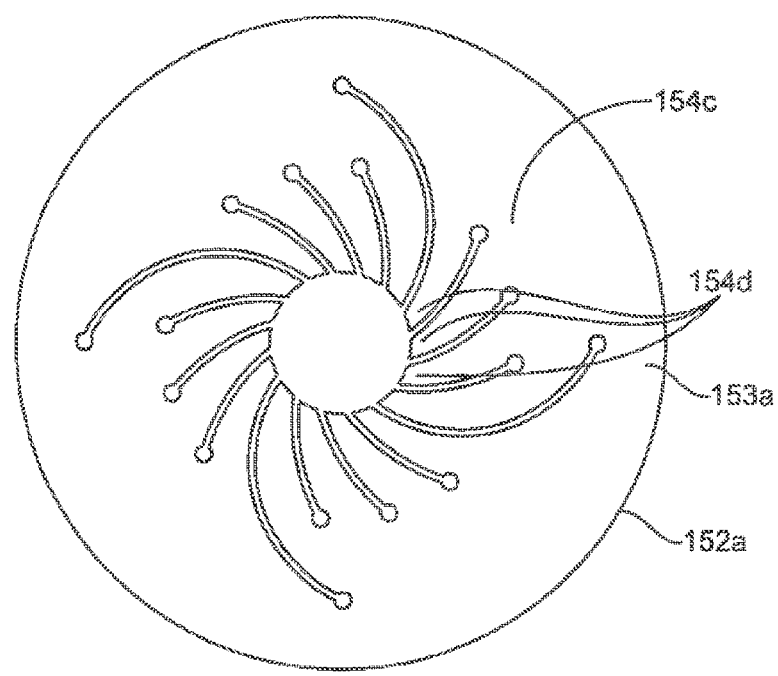
Figure 13E:
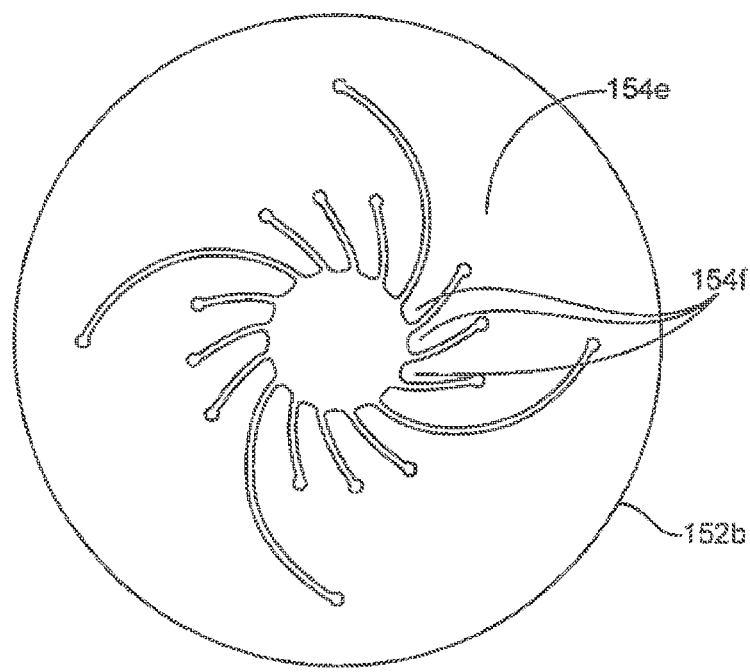

FIG. 13D is a plan view of an anti-inversion piece 152a. As shown, anti-inversion piece 152a includes several spiral-pattern fingers 154c that extend radially inward from outer perimeter 153a, and each spiral pattern finger 154c is divided into shorter spiral pattern subfingers 154d. As shown in FIG. 13L), there are four spiral pattern fingers 154c, each divided into four subfingers 154d. The cuts that define the spiral pattern fingers 154c extend radially outward to about 80-percent of anti-inversion piece 152a's radius, and the cuts that define the spiral pattern subfingers 154d extend radially outward to about 55-percent of anti-inversion piece 152a's radius. Other relative lengths between the fingers and subfingers may be used. For example, FIG. 13E is a plan view of an anti-inversion piece 152b. As shown in FIG. 13E, the cuts that define the spiral pattern fingers 154e extend radially outward to about 80-percent of anti-inversion piece 152b's radius, and the cuts that define the spiral pattern subfingers 154f extend radially outward to about 40-percent of anti-inversion piece 152b's radius. Thus in one aspect the length of cuts that define the subfingers is from about 40- to 55-percent for the radius, although other cut lengths may be used to define the fingers and subfingers. The spiral-patterned fingers and subfingers act to splay and twist out of the way when an instrument is inserted or withdrawn, and the subfingers' shorter range of motion during such splay and twist keeps the bent subfingers over the wiper seal sealing portion's upper annular face, which protects the annular face from sharp instrument tips.

Figure 13F:
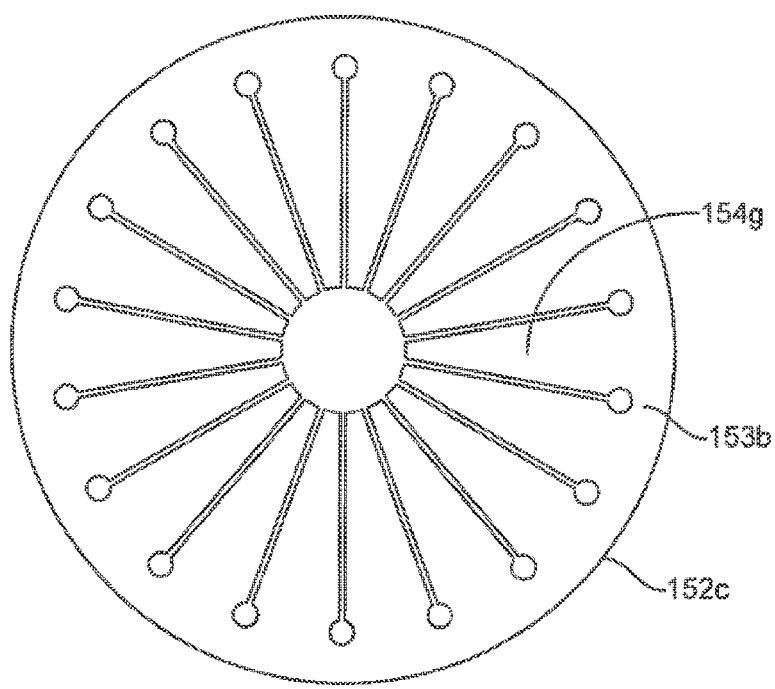
Figure 13G:
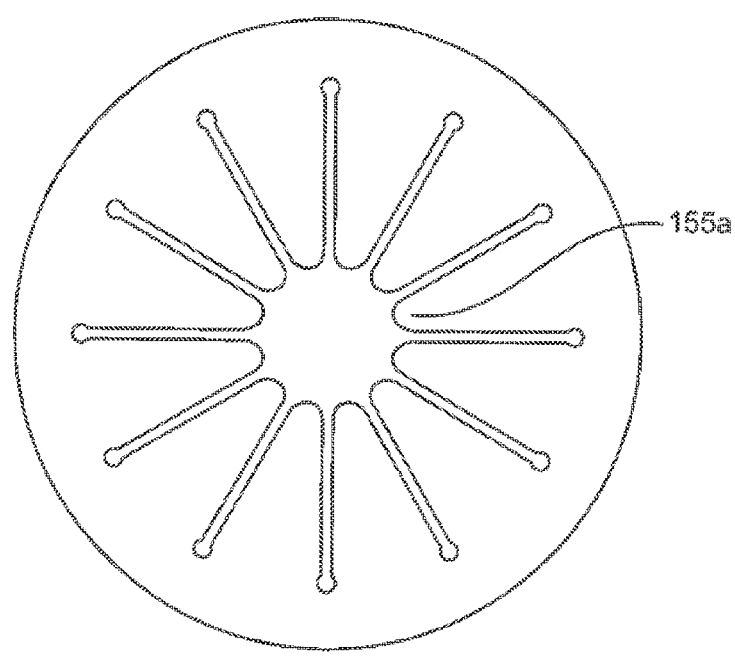
Figure 13H:
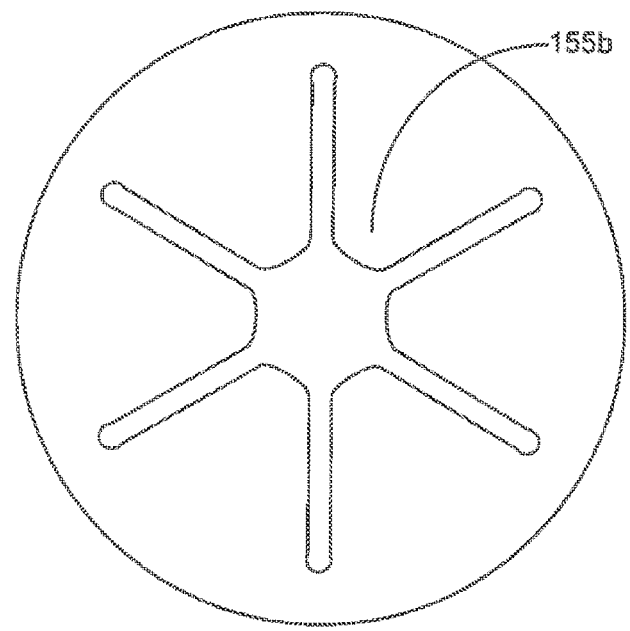

Although spiral pattern features in the anti-inversion piece have desirable characteristics, in other anti-inversion piece embodiments straight inward radial fingers may optionally be used. For example, FIG. 13F is a plan view of anti-inversion piece 152c with several equal-length straight fingers 154g that extend radially inward from outer perimeter area 153b. There are 18 fingers 154g shown in FIG. 13F, and other numbers of fingers may optionally be used. For example, FIG. 13G shows an implementation in which 12 straight radial fingers are used, and FIG. 13H shows an implementation in which 6 straight radial fingers are used. As shown in FIGS. 13F, 13G, and 13H, the radial cuts that define the fingers are relatively narrow, so that as the number of radial fingers decreases, the width of each individual finger correspondingly increases. Also, FIGS. 13G and 13H illustrate that the inner tips 155a (FIG. 13G) and 155b (FIG. 13H) may be rounded to help prevent catching on an instrument component as it is inserted and withdrawn through the anti-inversion piece, and to reduce friction against the instrument shaft.

Figure 13I:
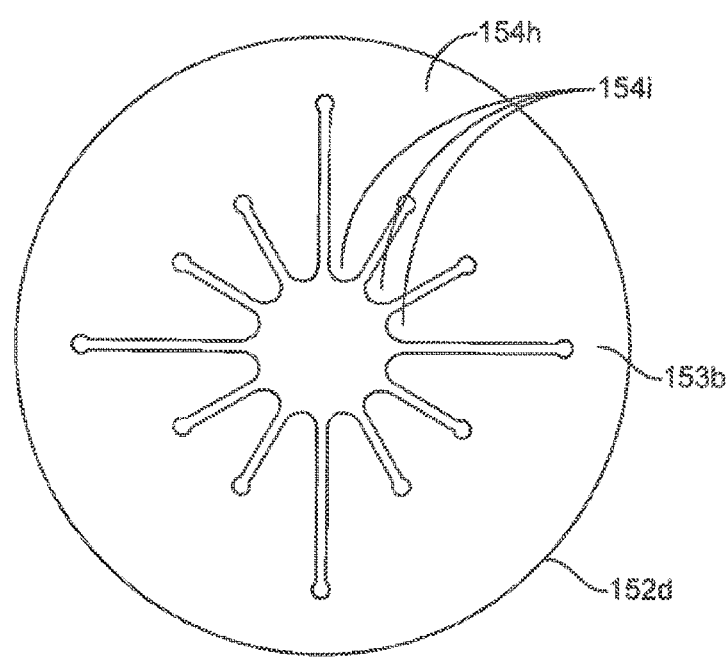

In addition, a finger and subfinger configuration as described above with reference to spiral-patterned fingers in FIGS. 13D and 13E may optionally be used for radially straight fingers. For example, FIG. 13I shows an anti-inversion piece 152d that includes several straight fingers 154h that extend inward from an outer perimeter area 153b, and each individual finger 154h is divided into subfingers 154i. As shown, anti-inversion piece 152d includes four fingers 154h, and each finger 154h includes three subfingers 154i. The cuts that define the fingers 154h extend to about 80-percent of anti-inversion piece 152d's radius, and the cuts that define the subfingers 154i extend to about 55-percent of anti-inversion piece 152's radius. Again, various other cut lengths may be used to define the fingers and subfingers.

Other Housing Features

FIG. 13B also illustrates two additional seal assembly housing features. As shown, seal assembly 151's housing optionally includes guards 157 that extend radially outward from the housing on either side of each latch finger tab 144.

Guards 157 help prevent the associated finger tab 144 from being inadvertently pressed inward to release the seal assembly from the cannula.

Also as shown in FIG. 13B, seal assembly 151's housing optionally includes two latch windows 158 on its top surface, and these windows are used to optionally latch another medical device, such as the obturator described below, to the housing's top surface, as explained above with reference to FIG. 2 and in more detail below. In addition, housing 151's top surface 151a is smooth and level along the arcs between the windows 158. This top surface configuration allows the component to be radially centered on the housing and rotated clockwise or counter-clockwise until the component's latches drop into the windows 158.

Obturator

Figure 14:
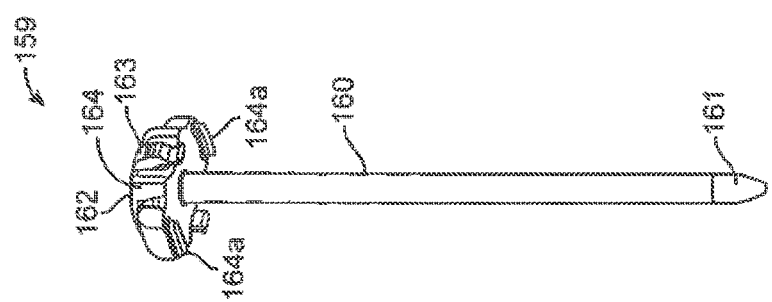
FIG. 14 is a perspective view of an example obturator.

FIG. 14 is a perspective view of an example obturator 159, which includes a shaft 160, a tip 161 at shaft 160's distal end, and a proximal portion 162 at shaft 160's proximal end. Two latches 163 are positioned on opposite sides of proximal portion 162, and these latches 163 are used to secure obturator 159 to the top of a seal assembly. Materials used for the obturator are similar to those used for the seal assembly.

Figure 15A:
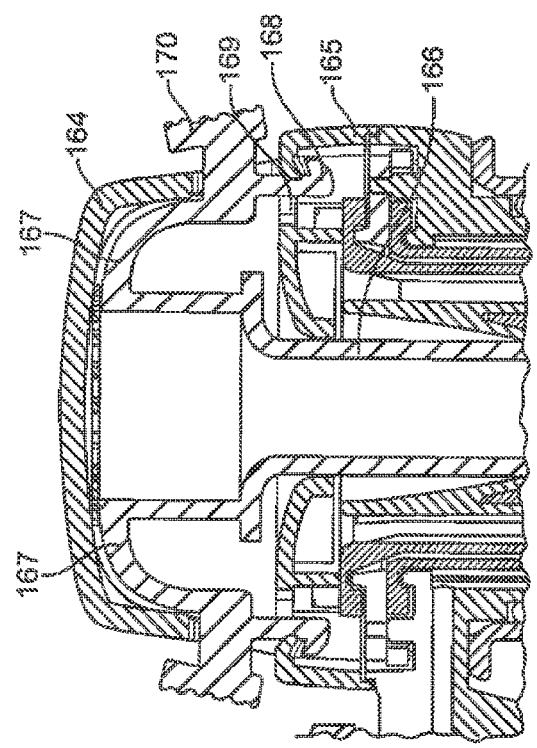
FIG. 15A is a cross-sectional view of a proximal portion of an example obturator coupled to the top of a seal assembly.

FIG. 15A is a cross-sectional view of a proximal portion 164 of an example obturator coupled to the top of a seal assembly 165. As shown in FIG. 15A, the obturator shaft 166 extends through seal assembly 165. Two resilient latch flexures 167 are positioned on opposite sides at obturator shaft 166's proximal end. At the far ends of the flexures 167 are catches 168, which insert through windows 169 in seal assembly 164's top surface and catch underneath the lips in the top portion of the seal assembly housing that define each window 169. The latches hold the obturator firmly against the seal assembly. Catches 168 are optionally beveled so that the obturator can be latched to the seal assembly by pressing it distally after the obturator is rotated to allow the catches to drop into the windows 158. The latch flexures 167 also include finger tabs 170, and by compressing the finger tabs 170 radially inwards, the catches 168 move radially inwards to allow the obturator to be removed from the seal assembly.

FIG. 153B is a cross-sectional view of the proximal portion 164 of the example obturator coupled to the top of seal assembly 165, taken at right angles to the view in FIG. 15A. The depicted seal assembly cross section is similar to the one illustrated in FIG. 12. FIG. 15B shows that obturator proximal portion 164 includes two distally projecting interference tabs 164a. When the obturator is fully seated on the seal assembly's top surface, each of these interference tabs 164 comes between the upper portion 165a of the seal assembly housing and the finger tab 144, thus preventing finger tab 144 from being pressed radially inward and consequently preventing the combination of the seal assembly and the obturator from being unlatched from the cannula flange 149a.

Referring to FIGS. 12 and 151, it can be seen that the latch piece 143 features allow the seal assembly to be securely latched to cannula 149, and also allow the seal assembly and any component coupled to it to rotate without limit around longitudinal axis A inside cannula 149. The cannula bowl flange 149a and seal assembly housing relief surface (shoulder) 150 are held between latch piece 143's finger 146 and catch 147, and cannula flange 149a's smooth underside allows catch 147 to move without interference, while the O-ring 165b maintains a gas-tight seal between the seal assembly and the cannula bowl's inner wall. One or more optional stops (not shown) may be placed on cannula flange 149a's underside to limit the amount that the seal assembly can rotate around the longitudinal axis in the cannula bowl. The seal assembly's ability to rotate in the cannula bowl provides an ability to orient the seal assembly's fluid entry/exit valve to any desired orientation, or to reorient the valve, as needed during use, as shown below. And, the ability to rotate the seal in the cannula bowl allows the seal to be initially latched to the cannula at various orientations, and then rotated as needed for use, so that perfect seal orientation alignment is not required for initial latching.

In one aspect, the combination of a cannula, the seal assembly, and an obturator is an assembly. The seal assembly enables the obturator to be coupled to the cannula. FIG. 16 is a perspective view of a medical device assembly 171 that includes a cannula 172, a seal assembly 173 latched to cannula 172, and obturator 174 latched to seal assembly 173 and extending through cannula 172 and seal assembly 173. The top (proximal end) of obturator 174 is rounded to accommodate the palm of the hand. In use, a surgeon inserts medical device assembly 171's distal end through a patient's body wall, and once medical device assembly 171 is inserted, the surgeon unlatches and withdraws obturator 174 from seal assembly 173 and cannula 172 so that other medical devices, such as an endoscope or a therapeutic surgical instrument, may be inserted through seal assembly 173 and cannula 172 to reach a surgical site.

In another aspect, a radially centered hole (not shown) is placed in obturator proximal portion 164, and at least the obturator tip 161 is made transparent. Such a transparent obturator tip is known. An endoscope is inserted through the radially centered hole and through obturator shaft 163 to obturator tip 161. The transparent obturator tip allows the surgeon to view insertion through the body wall. Thus, in one aspect, the combination of a cannula, the seal assembly, the obturator with a clear distal tip, and an endoscope inserted into the obturator is an assembly. The seal assembly enables the obturator to be coupled to the cannula.

As shown, cannula 172 is configured to be mounted on teleoperated medical device manipulator, part of a teleoperated surgical system, such as systems commercialized by Intuitive Surgical, Inc., Sunnyvale, Calif. In other implementations, however, medical device assembly 171, or any of its components, may be used for non-teleoperated surgical procedures, such as manual laparoscopy procedures.

Teleoperated Medical Device

Figure 17:
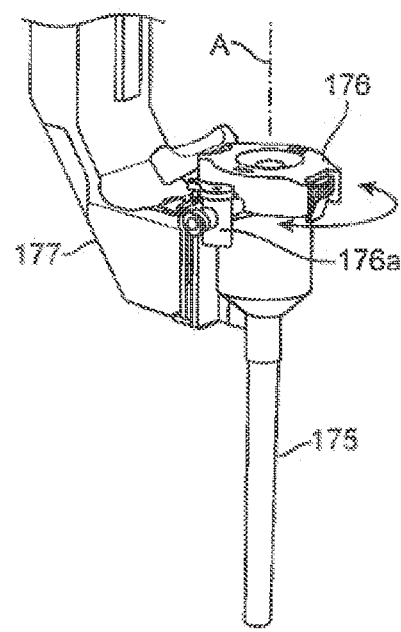
FIG. 17 is a perspective view of a cannula and seal assembly coupled together and mounted at the distal end of a teleoperated manipulator.

FIG. 17 is a perspective view of a cannula 175 and seal assembly 176 coupled together and mounted at the distal end of a teleoperated manipulator 177, which is part of a teleoperated surgical system. Seal assembly 176 is representative of the various seal assembly configurations described in this document. It can be seen that seal assembly 176's valve 176a can rotate clockwise or counter-clockwise within cannula 175, as indicated by the double-headed arrow. When several cannula 175 and seal assembly 176 are inserted into a patient in close proximity, each combination being docked with a corresponding manipulator 177, the ability to orient one or more of the valves 176a allows the associated tubing to be more easily coupled to a valve 176a, and also to be more effectively routed within the sterile field around the various other cannula entry ports into the patient. Further, the valve orientation can be changed while an instrument is inserted through the seal assembly and the cannula.

Figure 18:
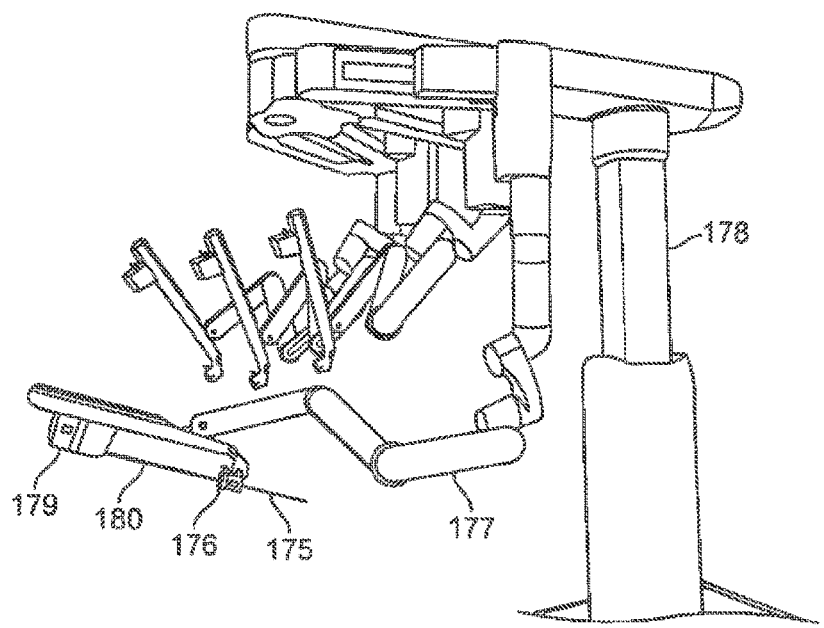
FIG. 18 is a perspective view of a teleoperated medical device 178 that incorporates a cannula and a seal assembly.

FIG. 18 is a perspective view of an example teleoperated medical device 178-a teleoperated surgical system (a portion of the patient-side component of a da Vinci Xi® Surgical System)—that incorporates at least one cannula 175 and seal assembly 176. As shown in FIG. 18, an example surgical instrument 179 is mounted at the distal end of manipulator 177, and surgical instrument 179's shaft 180 extends through seal assembly 176 and cannula 175. In some instances, one or more seal assemblies that accommodate one range of instrument shaft sizes (e.g., 5-8 mm) as described are each used with one or more corresponding instrument manipulator, and one or more other seal assemblies that accommodate another range of instrument shaft sizes (e.g., 10-12 mm) as described are used with one or more other corresponding manipulators.

It can be seen, therefore, that a seal assembly is an important component not just generally for minimally invasive surgical applications, but for allowing a teleoperated surgical system to operate effectively. As an example use, a seal assembly and cannula combination is mounted at the distal end of each of teleoperated medical device 178's depicted four manipulators, so that various surgical instruments may be inserted through one or more ports in a patient to reach a surgical site. A single seal assembly that accommodates various instrument shaft diameters allows teleoperated medical device 178 to simultaneously use various instruments with different shaft diameters, and using the same seal configuration for each cannula simplifies operation, because different seal assemblies that are dedicated to use with only one surgical instrument shaft diameter are not necessary. If necessary, therefore, surgical instruments with various diameters may be interchanged between two manipulators without a need for changing the seal assemblies for each cannula.

We claim:

1. A medical device comprising:
a seal assembly housing;
a wiper seal; and
a support rib;
the wiper seal including an outer perimeter portion at which the wiper seal is coupled to the seal assembly housing, an inner sealing portion, and a flex portion between the outer perimeter portion and the inner sealing portion, the flex portion including an annular corrugation and an annular groove defined by the annular corrugation, the support rib being positioned in the annular groove.

2. The medical device of claim 1:
the support rib comprising a first wall and a second wall, each of the first wall and the second wall including a first side and a second side opposite the first side, the first side of the first wall and the first side of the second wall each being coupled to the wiper seal, the second side of the first wall and the second side of the second wall each being coupled together and coupled to an outer wall of the annular groove.

3. The medical device of claim 1:
the support rib comprising a first wall and a second wall, each of the first and second walls including a first side and a second side opposite the first side, the first side of the first wall and the first side of the second wall each being coupled to an outer wall of the annular groove, the second side of the first wall and the second side of the second wall each being coupled together and coupled to the wiper seal.

4. The medical device of claim 1:
a location at which the support rib is coupled to an outer sidewall of the annular groove extending distal of a location at which the support rib is coupled to the wiper seal.

5. The medical device of claim 1:
the support rib including a first side and a second side opposite the first side, the support rib being coupled between an inner sidewall and an outer sidewall of the annular groove defined by the annular corrugation;
a location at which the support rib is coupled to the outer sidewall of the groove extending proximal of a location at which the support rib is coupled to the inner sidewall of the groove.

6. The medical device of claim 1:
the wiper seal comprising an angled upper annular face and an angled lower annular face that meet to form an annular seal lip.

7. The medical device of claim 1:
the angled upper annular face being at a first angle with reference to a longitudinal axis, the angled lower annular face being at a second angle with reference to the longitudinal axis, the first angle being less than the second angle; and
the longitudinal axis being defined between a top and a bottom of the seal assembly housing.

8. The medical device of claim 1, further comprising:
a cannula; and
an obturator including a top portion and a shaft;
the seal assembly housing being coupled to a proximal end of the cannula;
the obturator being coupled to a proximal portion of the seal assembly housing, and the shaft extending through the seal assembly housing and the cannula.

9. The medical device of claim 8 further comprising:
a surgical system including a manipulator;
the cannula being coupled to the manipulator.

10. The medical device of claim 1, further comprising:
an instrument insertion guide positioned between the wiper seal and the seal assembly housing, the instrument insertion guide being coupled to the wiper seal and laterally movable relative to the seal assembly housing.

11. A medical device comprising:
a seal assembly housing;
a wiper seal; and
at least one structural support;
the wiper seal including an outer perimeter portion at which the wiper seal is coupled to the seal assembly housing, an inner sealing portion, and a flex portion between the outer perimeter portion and the inner sealing portion, the flex portion including portions defining an annular groove between the flex portion and the outer perimeter portion, the at least one structural support being positioned in the annular groove.

12. The medical device of claim 11:
the at least one structural support comprising a first wall and a second wall, each of the first wall and the second wall including a first side and a second side opposite the first side, the first side of the first wall and the first side of the second wall each being coupled to the wiper seal, the second side of the first wall and the second side of the second wall each being coupled together and coupled to an outer wall of the annular groove.

13. The medical device of claim 11:
the at least one structural support comprising a first wall and a second wall, each of the first and second walls including a first side and a second side opposite the first side, the first side of the first wall and the first side of the second wall each being coupled to an outer wall of the annular groove, the second side of the first wall and the second side of the second wall each being coupled together and coupled to the wiper seal.

14. The medical device of claim 11:
a location at which the at least one structural support is coupled to an outer sidewall of the annular groove extending distal of a location at which the at least one structural support is coupled to the wiper seal.

15. The medical device of claim 11:
the at least one structural support including a first side and a second side opposite the first side, the at least one structural support being coupled between an inner sidewall and an outer sidewall of the annular groove defined by the annular corrugation;
a location at which the at least one structural support is coupled to the outer sidewall of the groove extending proximal of a location at which the at least one structural support is coupled to the inner sidewall of the groove.

16. The medical device of claim 11:
the wiper seal comprising an angled upper annular face and an angled lower annular face that meet to form an annular seal lip.

17. The medical device of claim 11:
the angled upper annular face being at a first angle with reference to a longitudinal axis, the angled lower annular face being at a second angle with reference to the longitudinal axis, the first angle being less than the second angle; and
the longitudinal axis being defined between a top and a bottom of the seal assembly housing.

18. The medical device of claim 11, further comprising:
a cannula; and
an obturator including a top portion and a shaft;
the seal assembly housing being coupled to a proximal end of the cannula;
the obturator being coupled to a proximal portion of the seal assembly housing, and the shaft extending through the seal assembly housing and the cannula.

19. The medical device of claim 18 further comprising:
a surgical system including a manipulator;
the cannula being coupled to the manipulator.

20. The medical device of claim 11, further comprising:
an instrument insertion guide positioned between the wiper seal and the seal assembly housing, the instrument insertion guide being coupled to the wiper seal and laterally movable relative to the seal assembly housing.

* * * * *

UNITED STATES PATENT AND TRADEMARK OFFICE
CERTIFICATE OF CORRECTION

| | | |
|---|---|---|
| PATENT NO. | : 11,534,205 B2 | Page 1 of 1 |
| APPLICATION NO. | : 16/592406 | |
| DATED | : December 27, 2022 | |
| INVENTOR(S) | : Reid et al. | |

It is certified that error appears in the above-identified patent and that said Letters Patent is hereby corrected as shown below:

On the Title Page

Item (57), in "Abstract", in Column 2, Line 1, delete "us" and insert --use-- therefor Signed and Sealed this
Twenty-eighth Day of February, 2023

Katherine Kelly Vidal
*Director of the United States Patent and Trademark Office*